(12) United States Patent
Arantes et al.

(10) Patent No.: US 11,037,573 B2
(45) Date of Patent: Jun. 15, 2021

(54) MANAGEMENT AND EXECUTION OF EQUIPMENT MAINTENANCE

(71) Applicant: HITACHI, LTD., Tokyo (JP)

(72) Inventors: Adriano Siqueira Arantes, San Jose, CA (US); Marcos Vieira, San Francisco, CA (US); Chetan Gupta, San Mateo, CA (US); Ahmed Khairy Farahat, Santa Clara, CA (US); Maria Teresa Gonzalez Diaz, Mountain View, CA (US)

(73) Assignee: HITACHI, LTD., Tokyo (JP)

( * ) Notice: Subject to any disclaimer, the term of this patent is extended or adjusted under 35 U.S.C. 154(b) by 168 days.

(21) Appl. No.: 16/121,837

(22) Filed: Sep. 5, 2018

(65) Prior Publication Data

US 2020/0075027 A1 Mar. 5, 2020

(51) Int. Cl.
| | |
|---|---|
| *G10L 15/22* | (2006.01) |
| *G10L 17/22* | (2013.01) |
| *G06N 20/00* | (2019.01) |
| *G10L 13/00* | (2006.01) |
| *G10L 17/00* | (2013.01) |
| *G06Q 10/00* | (2012.01) |
| *H04N 1/00* | (2006.01) |

(Continued)

(52) U.S. Cl.
CPC .............. *G10L 17/22* (2013.01); *G06N 20/00* (2019.01); *G06Q 10/20* (2013.01); *G10L 13/00* (2013.01); *G10L 17/00* (2013.01); *G06F 16/9535* (2019.01); *G10L 25/63* (2013.01); *G10L 2015/227* (2013.01); *H04N 1/00344* (2013.01)

(58) Field of Classification Search
None
See application file for complete search history.

(56) References Cited

U.S. PATENT DOCUMENTS

| | | | |
|---|---|---|---|
| 5,729,452 A | 3/1998 | Smith et al. | |
| 6,298,305 B1 | 10/2001 | Kadaba et al. | |
| 6,990,458 B2 * | 1/2006 | Harrison | G06Q 10/06311 705/7.14 |
| 8,223,374 B2 * | 7/2012 | Katou | H04N 1/00344 358/1.15 |
| 9,672,497 B1 * | 6/2017 | Lewis | G06F 40/284 |
| 10,268,677 B2 * | 4/2019 | Lei | G06F 40/30 |

(Continued)

FOREIGN PATENT DOCUMENTS

| | | |
|---|---|---|
| JP | 2003215985 A | 7/2003 |
| JP | 2005352154 A | 12/2005 |

(Continued)

OTHER PUBLICATIONS

Extended European Search Report received in corresponding European Application No. 19160748.0 dated Sep. 23, 2019.

(Continued)

*Primary Examiner* — Richard Z Zhu
(74) *Attorney, Agent, or Firm* — Mattingly & Malur, PC

(57) ABSTRACT

In some examples, a system may receive from a device, speech sound patterns corresponding to a voice input related to equipment. Further, the system may determine an identity of a person associated with the device, and may identify the equipment related to the voice input. Using at least one of the received speech sound patterns or a text conversion of the speech sound patterns, along with an equipment history of the identified equipment, as input to one or more machine learning models, the system may determine, at least partially, an instruction related to the equipment. Additionally, the system may send, to the device, the instruction related to the equipment as an audio file for playback on the device.

25 Claims, 14 Drawing Sheets

| Initiator | Input Type | Output Type | Severity Level | Action Instruction Type |
|---|---|---|---|---|
| Operator | Comment (E.G., Observation, Complaint, Report) | Easy-to-understand natural language instruction by voice to operator | High, Medium, or Low | Ignore, Quick Fix, or Repair |
| Equipment | Sensor Data and/or Event Notification | Easy-to-understand natural language instruction by voice to operator and/or control signal to equipment | High, Medium, or Low | Ignore, Quick Fix, or Repair |

(51) Int. Cl.
*G06F 16/9535* (2019.01)
*G10L 25/63* (2013.01)

(56) References Cited

U.S. PATENT DOCUMENTS

| | | | |
|---|---|---|---|
| 2003/0004908 A1* | 1/2003 | Linthicum | G06F 30/00 706/45 |
| 2003/0167167 A1* | 9/2003 | Gong | G10L 15/22 704/250 |
| 2008/0254746 A1 | 10/2008 | Krishnan et al. | |
| 2009/0323103 A1* | 12/2009 | Katou | H04N 1/00344 358/1.15 |
| 2010/0229112 A1* | 9/2010 | Ergan | G06F 11/0748 715/764 |
| 2011/0119062 A1 | 5/2011 | Dohan | |
| 2015/0371455 A1* | 12/2015 | Abdel-Rahman | G06Q 10/20 701/29.1 |
| 2016/0189709 A1 | 6/2016 | Stepanski et al. | |
| 2016/0342681 A1* | 11/2016 | Kesin | G06F 16/367 |
| 2017/0031997 A1* | 2/2017 | Merg | G06F 16/24575 |
| 2017/0270922 A1 | 9/2017 | Fu | |
| 2019/0102685 A1* | 4/2019 | Foster | G06F 40/30 |

FOREIGN PATENT DOCUMENTS

| | | |
|---|---|---|
| JP | 2008310579 A | 12/2008 |
| JP | 201011434 A | 1/2010 |
| JP | 2014164482 A | 9/2014 |
| JP | 2015085533 A | 5/2015 |
| JP | 2017138509 A | 8/2017 |

OTHER PUBLICATIONS

William Chan, et al., Listen, Attend and spell: A neural network for large vocabulary conversational speech recognition, IEEE 2016, p. 4960-4964.
Alex Graves, et al., Speech Recognition with deep recurrent neural networks, Department of Computer Science, University of Toronto, Mar. 2013.
PCT Application PCT/US2017/055461 filed Oct. 6, 2017.
International Search Report of PCT/US2017/055461 dated Jan. 5, 2018.
Japanese Office Action received in corresponding Japanese Application No. 2019-049204 dated Jun. 16, 2020.

* cited by examiner

| Initiator | Input Type | Output Type | Severity Level | Action Instruction Type |
|---|---|---|---|---|
| Operator | Comment (e.g., observation, complaint, report) | Easy-to-understand natural language instruction by voice to operator | High, Medium, or Low | Ignore, Quick Fix, or Repair |
| Equipment | Sensor Data and/ or Event Notification | Easy-to-understand natural language instruction by voice to operator and/or control signal to equipment | High, Medium, or Low | Ignore, Quick Fix, or Repair |

FIG. 3

| Event ⟋402 | Component ⟋404 | Conf % ⟋406 | Part ⟋408 | Conf % ⟋410 | Action Type ⟋412 | Conf % ⟋414 |
|---|---|---|---|---|---|---|
| Water Pump Leak | Cooling | 100 | Water Pump Assembly | 100 | Replace | 95 |
| Engine Noise | Power Plant | 100 | Engine Assembly Parts | 90 | Diagnose | 85 |

FIG. 4

| Equipment ID ~502 | Make ~504 | Model ~506 | Year ~508 | Leased ~510 | Mileage ~512 | Engine Size ~514 |
|---|---|---|---|---|---|---|
| EQ1087 | Ford | Focus | 2017 | No | 10389 | 2.0 L |
| EQ0892 | Toyota | Yaris | 2018 | Yes | 3987 | 1.5 L |
| ... | ... | ... | ... | ... | ... | ... |

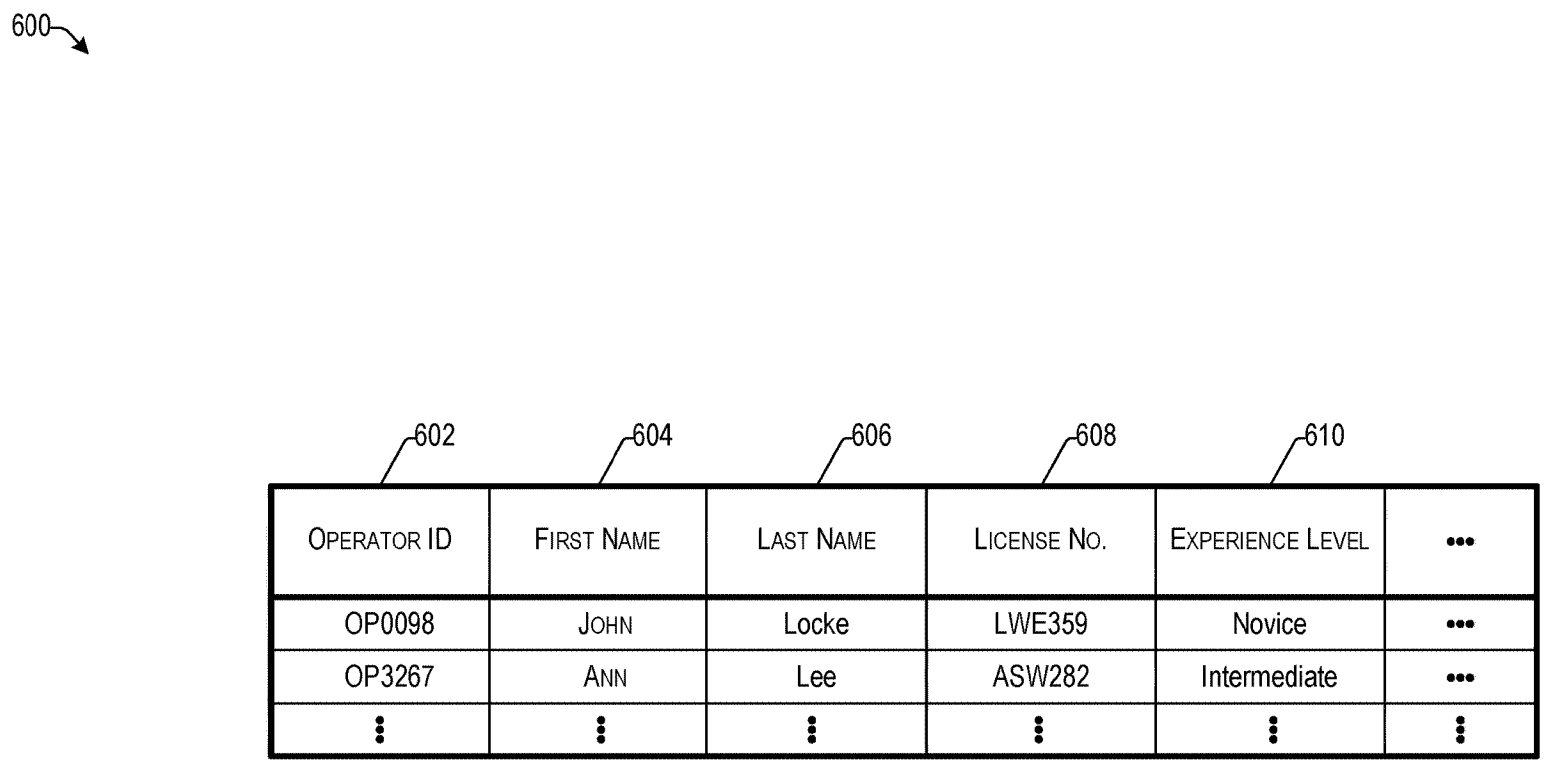

| OPERATOR ID | FIRST NAME | LAST NAME | LICENSE NO. | EXPERIENCE LEVEL | ... |
|---|---|---|---|---|---|
| OP0098 | JOHN | Locke | LWE359 | Novice | ... |
| OP3267 | ANN | Lee | ASW282 | Intermediate | ... |
| ... | ... | ... | ... | ... | ... |

FIG. 6

| Repair Site ID (702) | Name (704) | City (706) | GPS Latitude (708) | GPS Longitude (710) |
|---|---|---|---|---|
| RS002 | Economy Auto Repair | Sunnyvale, CA | 37.367548 | 121.996734 |
| RS087 | JP Automotive | San Jose, CA | 37.302793 | 122.031919 |
| ... | ... | ... | ... | ... |

FIG. 7

| LOCATION ID | TEMPERATURE | HUMIDITY | VISIBILITY | CONDITION | ... |
|---|---|---|---|---|---|
| LO000231 | 48 | 51 | 10 | Sunny | ... |
| LO001358 | 30 | 73 | 5 | Freezing Rain | ... |
| ... | ... | ... | ... | ... | ... |

FIG. 8

| PART ID ~902 | NAME ~904 | SUPPLIER ~906 | DESCRIPTION ~908 | COMPONENT/ ASSEMBLY ~910 | INVENTORY ~912 |
|---|---|---|---|---|---|
| PA00012 | PISTON RING | Delphi | Piston ring for engine | Engine Block | 10389 |
| PA00032 | COIL – AC CLUTCH | Ford | Coil for AC | Air Conditioner | 3987 |
| PA0177 | SPARK PLUG | Bosh | Spark Plug for Ignition | Engine Head | 3987 |
| ... | ... | ... | ... | ... | ... |

| TECHNICIAN ID | FIRST NAME | LAST NAME | LEVEL | SPECIALIST | SKILLS | ... |
|---|---|---|---|---|---|---|
| TC9452 | KATE | Austin | Senior | Ford | Engine, Transmission | ... |
| TC3710 | HUGO | Reyes | Junior | GM | Suspension, Brakes | ... |
| ... | ... | ... | ... | ... | ... | ... |

FIG. 10

MANAGEMENT AND EXECUTION OF EQUIPMENT MAINTENANCE

BACKGROUND

The objective of equipment maintenance is to keep the equipment in an operative, efficient, and cost-effective condition. The maintenance process is conducted by performing actions on the equipment to achieve one or more of these objectives. These actions may include, but are not limited to, inspecting, tuning, calibrating, repairing, and/or overhauling the equipment. Maintenance may typically be performed according to a prescribed schedule. However, the typical maintenance schedule may not take into account the current condition and the unique history of an individual piece of equipment. Furthermore, when an unexpected problem with the equipment is detected in the field, it may be difficult for an equipment operator to determine a proper course of action to take.

SUMMARY

Some implementations include arrangements and techniques for managing equipment. In some examples, the system may receive, from a device, speech sound patterns corresponding to a voice input related to the equipment. Further, the system may determine an identity of a person associated with the device, and may identify the equipment related to the voice input. Using at least one of the received speech sound patterns or a text conversion of the speech sound patterns, along with an equipment history of the identified equipment, as input to one or more machine learning models, the system may determine, at least partially, an instruction related to the equipment. Additionally, the system may send, to the device, the instruction related to the equipment as an audio file for playback on the device.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 3 illustrates an example data structure showing an action instruction summary according to some implementations.

FIG. 4 illustrates an example data structure including a detailed action instruction for a technician according to some implementations.

FIG. 5 illustrates an example data structure showing fleet management data for an equipment identifier (ID) according to some implementations.

FIG. 6 illustrates an example data structure including customer relationship management data for an operator according to some implementations.

FIG. 7 illustrates an example data structure showing repair site fleet management data according to some implementations.

FIG. 8 illustrates an example data structure showing weather sample data according to some implementations.

FIG. 9 illustrates an example data structure showing parts data according to some implementations.

FIG. 10 illustrates an example data structure showing technician information according to some implementations.

DETAILED DESCRIPTION

Figure 1:
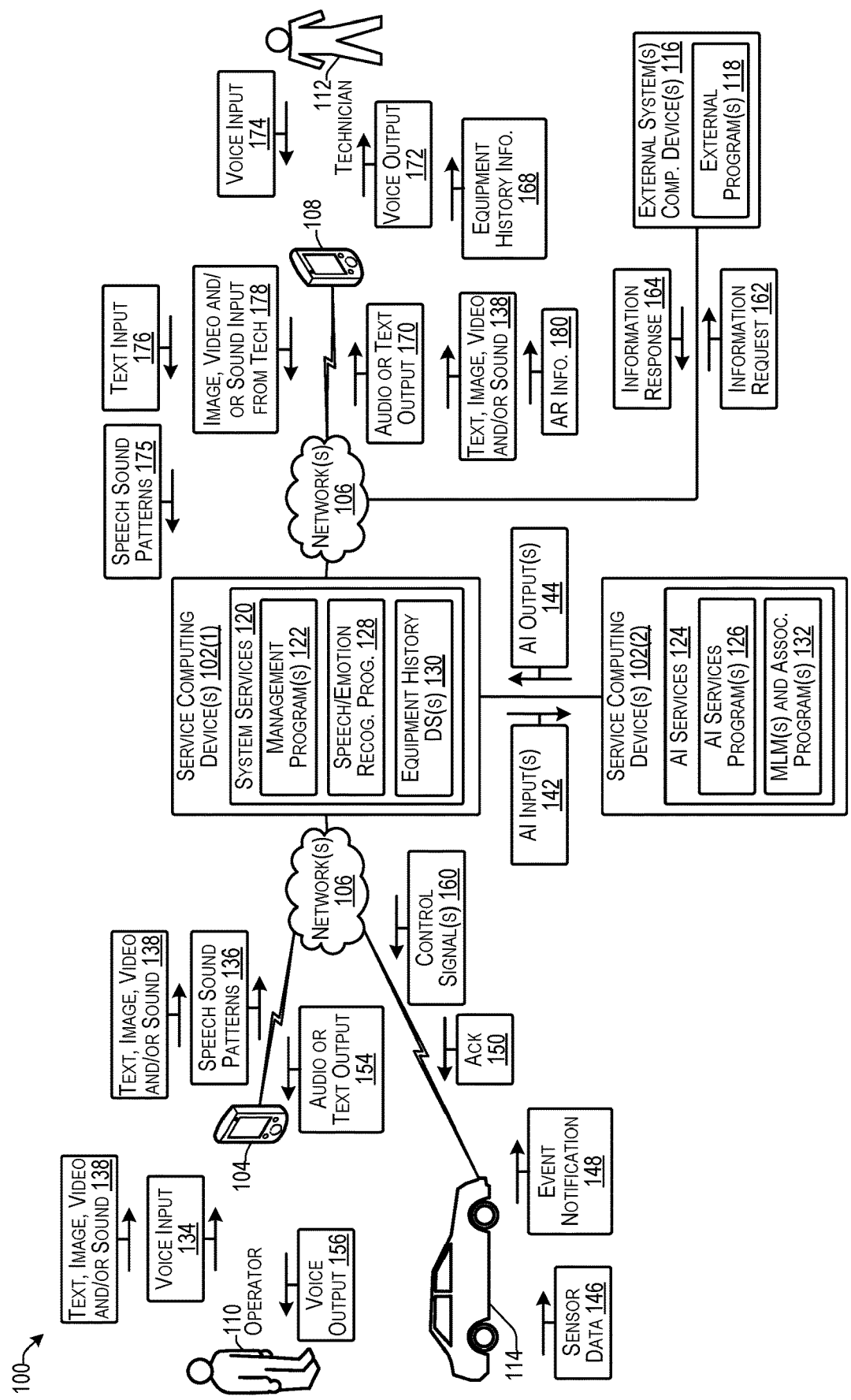
FIG. 1 illustrates an example configuration of a system able to manage and maintain equipment according to some implementations.

Some implementations herein are directed to techniques and arrangements that use artificial intelligence (AI), machine learning, and speech/emotion recognition in a system for enabling communications with operator devices, technician devices, and/or external systems managing equipment and associated maintenance of the equipment. For instance, the system may enable natural language voice commands to and from an equipment operator in the field, and/or to and from an equipment technician to increase usage and effectiveness of the system, such as for performing management, maintenance, and/or repair of equipment. As one example, the system may acquire voice inputs as natural language inputs to the system through an operator device. The system allows users to ask questions and receive answers using voice communications for communicating with AI systems, such as for repair recommendations, failure predictions, and operation optimization.

Implementations herein may use speech-to-text conversion based on a natural language input to the system, such as for equipment management or maintenance. In addition to recognizing speech, the system may be reactive to user pitch, tone, timbre, cadence, emphasis, stress, etc., to determine and classify an emotion that may be present in a received speech pattern. The system may provide for equipment instruction and/or maintenance in an industry scenario using voice as the main user interface. For instance, voice may be used as both an input to and an output from machine learning models for communicating with operators and/or technicians, such as for enabling interactions, e.g., at the current location of the equipment in the field, or at a designated repair site, that would be difficult or unsafe to be performed previously. Further, the system may provide real-time recommendations or other instructions based on analysis performed using the machine learning models. Accordingly, the system may provide a natural user experience through voice communications and an integrated end-to-end maintenance and operational experience based on machine learning techniques.

The system for equipment management and maintenance herein may integrate field operation and repair site maintenance. For instance, users of the system may include equipment end-users and other equipment operators; maintenance personnel, equipment management personnel, and other equipment technicians; and organization decision makers and operation managers. The functions provided to the aforementioned users may include logging observations or otherwise reporting problems with equipment; receiving instructions for actions based on observations or other reported problems, such as, ignore, quick fix, and/or repair instructions when the equipment is being operated on the field; determining instructions for actions to be implemented based on real-time sensor data coming from the equipment on the field; determining repair actions when the equipment fails or is brought to a maintenance site; reducing diagnosis time, repair time, and repair mistakes, and thereby increasing the overall availability of the equipment and improving worker productivity. The system herein may be used as a standalone solution or may be integrated with other existing systems that provide other functionalities for equipment maintenance, management, and optimization.

For discussion purposes, some example implementations are described in the environment of a computer system that determines instructions and/or actions for managing or maintaining equipment. However, implementations herein are not limited to the particular examples provided, and may be extended to other types of equipment, other environments of use, other system architectures, other applications, and so forth, as will be apparent to those of skill in the art in light of the disclosure herein.

FIG. 1 illustrates an example configuration of a system 100 able to manage and maintain equipment according to some implementations. The system 100 includes at least one service computing device 102 that is able to communicate directly or indirectly with an operator device 104, such as over one or more networks 106. In addition, the service computing device(s) 102 may communicate over the one or more networks 106 with a technician device 108. The operator device 104 may be associated with an operator 110 and the technician device 108 may be associated with a technician 112. In addition, the service computing device(s) 102 may be able to communicate over the one or more networks 106 with equipment 114 and one or more external systems computing devices 116, each of which may include a respective external program 118.

The one or more networks 106 may include any type of network, including a LAN, such as an intranet; a WAN, such as the Internet; a wireless network, such as a cellular network; a local wireless network, such as Wi-Fi; short-range wireless communications, such as BLUETOOTH®; a wired network including fiber optics, Ethernet, Fibre Channel, or any other such network, a direct wired connection, or any combination thereof. Accordingly, the one or more networks 106 may include both wired and/or wireless communication technologies. Components used for such communications can depend at least in part upon the type of network, the environment selected, or both. Protocols for communicating over such networks are well known and will not be discussed herein in detail. Accordingly, the service computing device(s) 102, the operator device 110, the technician device 108, the equipment 114, and the external system(s) computing device(s) 116 are able to communicate over the one or more networks 106 using wired or wireless connections, and combinations thereof.

Furthermore, while a single operator device 104, operator 110, technician device 108, technician 112, and equipment 114 are illustrated in this example for clarity of illustration, in actual operation, there may be a large number of operator devices 104, operators 110, technician devices 108, technicians 112, and equipment 114 participating in the system 100. Accordingly, implementations herein are not limited to any particular number of operator devices 104, operators 110, technician devices 108, technicians 112, and equipment 114.

In the illustrated example, the service computing device(s) 102 include one or more first service computing devices 102(1) and one or more second service computing devices 102(2). The first service computing device(s) 102(1) may include system services 120, such as by executing one or more management program(s) 122. Furthermore, the second service computing device(s) 102(2) may include AI services 124, such as by executing one or more AI services programs 126. Additionally, while the system services 120 and the AI services 124 are illustrated as being executed on separate service computing devices 102 in this example, in other examples, these services may be distributed in any desired manner across any number of service computing devices 102. For instance, the system services 120 and the AI services 124 may be executed on the same service computing device 102 in some cases. In other cases, the AI services and the system services may be spread across more than two service computing devices 102.

In the example system 100 illustrated in FIG. 1, the operator 110 may be a user of the equipment 114, i.e., the operator 110 may be operating the equipment 114, such as at a worksite, construction site, along an operation route, or other location of operation, e.g., in the field, depending on the type of the equipment 114. Further, the equipment 114 may be any type of machine, vehicle, apparatus, or the like, that may be operated by the operator and that may be subject to maintenance, repair, or the like. Several non-limiting examples of common types of equipment according to some implementations herein may include cars, trucks, motorcycles, conveying belts, cranes, trains, tractors, airplanes, construction vehicles, construction machines, power generation equipment, manufacturing equipment, robots, electronics, and various other types of machines. In addition, the technician 112 may be an engineer, mechanic, technical specialist, or other person who has training or other skills for evaluating an equipment condition or state and determining one or more actions based on the evaluation, such as for performing maintenance, repair, or otherwise putting the equipment into a condition in which the operator is able to continue to use the equipment 114.

The operator device 104 and the technician device 108 may be computing devices or other communication devices to enable voice communication with the service computing device(s) 102 over the one or more networks 106. In some examples, the devices 104 and 108 may provide multiple communication modes for interacting with the system 100. For instance, the devices 104, 108 may provide multiple tools to enable users to input data to the system 100 and receive data output from the system 100. Examples of such data may include images, text, speech, touch, fingerprints, video, sounds, virtual and augmented reality, and the like. Several non-limiting examples of the devices 104, 108 include smartphones, tablet computing devices, intercoms, microphones, speakers, recorders, cameras, augmented or virtual reality equipment (glasses, headsets, etc.), laptop computers, desktop computers, computer terminals, pagers, smart pens, and so forth.

As mentioned above, the service computing device(s) 102(1) may execute the management program(s) 122 to provide the system services 120. The management program(s) 122 may access a speech and/or emotion recognition program 128 for converting received speech to text. Further, in some cases, the emotions associated with the received speech may also be detected and used when formulating a response to a user. Further, the management program(s) 122 may provide a set of services to integrate and communicate with different systems and/or system components and/or subcomponents over the one or more networks 106, such as through a communication protocol for executing a task. A non-exhaustive listing of several example tasks may include querying or storing information in a database or other data structure, such as in one or more equipment history data structures (DSs) 130; communicating with and obtaining information from the external system(s) computing device(s) 116; sending notifications or other communications to users, such as the operator 110 or the technician 112; acquiring insights or other information about data based on rules and/or based on using artificial intelligence and machine learning.

The AI services 124 may include one or more trained machine learning models (MLMs) and associated programs (e.g., model building and training programs) 132 that may be used to make decisions and provide instructions for actions to be taken for particular equipment 114. The system services 120 in the system 100 may employ a modular approach by using a plurality of programs and computing devices that allow the system 100 to scale depending on the use case. For instance, one or more application programming interfaces (APIs) (not shown in FIG. 1) may be employed to enable the various programs and applications herein to interact with each other for communicating and processing information related to the equipment 114.

The AI services program(s) 126 may be executed to provide the AI services 124. For example, the AI services 124 may include a plurality of AI solutions as the MLM(s) and associated programs 132, such as for failure prediction, repair recommendation, operations optimization, and so forth. The one or more APIs may be employed to access a plurality of respective programs and associated machine learning models (MLMs) for enabling the plurality of AI solutions.

In addition, the management program(s) 122 may communicate with one or more external systems by communicating with the one or more external systems computing devices 116. For instance, the management program(s) 122 (or in some cases the AI services program(s) 122) may contact the external system(s) computing device(s) 116 to improve the overall knowledge of the system 100 by accessing other data sources or services available from the external systems. Additionally, in some examples, the management program(s) 122 may access the external systems, such as to order parts, schedule towing, schedule maintenance, or the like. In some instances, the management program(s) 122 may employ the one or more APIs to access various different types of external systems such as a customer relationship management system, a fleet management system, a towing and rental system, an order and parts systems, a weather data system, a road conditions system, and so forth.

By combining all of the above-discussed features into a distributed computing system, the system 100 may perform operations that include, but are not limited to: improving equipment and operation usage in the field; reducing repair time at a maintenance location; increasing repair efficiency at the maintenance repair site; enhancing user confidence regarding AI system outputs, such as by adding voice interactions; and improving system-user communications by using voice as input and output to an AI system.

As one example, suppose that the operator 110 notices a loud noise coming from the engine of a vehicle, which is the equipment 114 that that operator 110 is currently operating. The operator 110, through speaking to the operator device 104, may use his/her voice, to make an observation, complaint, comment, request status information about the equipment 114, or the like, as a voice input 134. For example, a microphone (not shown in FIG. 1) associated with the operator device 104 may receive the speech of the voice input 134, and may transmit immediately to the service computing device(s) 102(1). For instance, the operator device 104 may send the received speech sound patterns 136 to the service computing device(s) 102.

In addition, if the operator 110 also provides text, image, video, and/or sound 138 via the operator device 104, the operator device 104 may forward the text, image, video and/or sound 138 to the service computing device(s) 102. In some examples, before providing the voice input 134, the operator 110 may open a client application (not shown in FIG. 1) on the operator device 104, and the operator 110 may issue the voice input 134 via the operator device 104. For example, the operator 110 may use natural language to describe the problem with the equipment 114. Additionally, in some cases, the client application may be configured to run constantly in the background, such as listening for a keyword or the like to trigger sending of speech sound patterns 136 to the service computing device 102.

The management program(s) 122 receives the voice sound waves produced by the operator 110 as the speech sound patterns 134 and may store the speech sound patterns in association with one or more of the equipment history data structures 130. For example, the management program(s) 122 may maintain the one or more equipment history data structures 133 for tracking the individual history of each equipment 114 managed by the system 100, and may maintain a history of maintenance actions, failures, event notifications from the equipment, received sensor data from the equipment, operator complaints or other operator comments, technician comments, and so forth. If the operator 110 also provides one or more of text, image, video, and/or sound 138, this information may also be stored in one or more of the equipment history data structures 130.

In response to receipt of the speech sound patterns 134, the management program(s) 122 may use the speech and/or emotion recognition program 128 to perform automated speech recognition for translating the received speech to text. Additional details of the speed and/or emotion recognition performed herein are described below, e.g., with respect to FIG. 13. The speech-to-text translation may be used to provide one or more AI inputs 142 to the AI services 124. The AI input(s) 142 may be applied as an input to one or more of the previously trained machine learning models and associated programs 132 for providing, as one or more AI outputs 144, instructions on an action to be taken by the operator 110 in response to the complaints or other comments from the operator 110 with respect to the equipment 114.

In addition, the equipment 114 may include one or more sensors (not shown in FIG. 1) and may obtain sensor data 146 that may be analyzed either at the equipment 114 itself, or may be sent to the management program(s) 122 for analysis to detect any problems with the equipment 114. For instance, suppose that the equipment 114 or an associated processor (not shown in FIG. 1) performs edge processing on the sensor data 146 to detect whether there are any problems with the equipment 114. When a problem is detected based on the sensor data 146, the equipment 114 may send an event notification 148 to the management program(s) 122. In some cases, equipment 114 may also send the sensor data 146 that caused the event notification 148 to be sent. In response to the event notification 148, the management program(s) 122 may send an acknowledgment 150 to the equipment 114 to acknowledge receipt of the event notification 148 indicating the problem with the equipment 114. Any sensor data 146 received from the equipment 114, as well as any event notifications 148 may be stored in the equipment history data structure(s) 130.

Alternatively, of course, the equipment 114 may just send the sensor data 146 to the service computing device(s) 102(1), and the management program(s) 122 may determine whether there is a problem, such as by providing the sensor data 146 to the AI services 124, or through various other techniques. Further, the management program(s) 122 may store and received sensor data 146 and an indication of a detected event in the one or more equipment history data structures 130.

In either event, in response to the AI output(s) 144 or in response to otherwise detecting an event at the equipment 114, the management program(s) 122 may send an audio or text output 154 to the operator device 104. For example, the audio or text output 154 may include a compressed or uncompressed audio file for playback by the operator device 104, such as a WAV file, MP3 file, AIFF file, AAC file, WMA file, MPEG-4 file, and so forth. The operator device 104 may provide a voice output 156 that is audible to the operator 110. In some cases, receipt of the audio file may cause a client application on the operator device 104 to automatically play or otherwise present the audio file, such as on one or more speakers (not shown in FIG. 1) associated with the operator device 104.

In addition, in some examples, the operator device 104 may present a text version of the voice output 156 on a display or the like associated with the operator device 104. In some example, the operator device 104 may include a client application (not shown in FIG. 1) executing on the operator device 104 that may receive a text output rather than an audio output as the audio or text output 154, and that may translate the text output into the natural language voice output 156 that may be played over the speakers of the operator device 104 or otherwise presented to the operator 110. Additionally, in some examples, the voice output 156 may include a request for more information or a request for confirmation that the operator 110 is aware of the problem with the equipment 114, or the like.

As one example, suppose that the operator 110 says while using the equipment "I hear a loud noise coming from the engine". The operator's comment is received by the operator device 104 as a voice input 134, which is sent to the management program(s) 122 as a speech sound pattern 136. The management program(s) 122 may have received sensor data 146 from the equipment 114, or may request sensor data 146 from the equipment 114 in response to receiving the speech sound pattern 136 and determining the speech-to-text thereof. The management program(s) 122 may provide the comment and the sensor data 146 as AI inputs 142 to the AI services 124. In response, the management program(s) 122 may receive an AI output 144 from the AI services 124. Based on the AI output 144, the management program(s) 122 may provide audio text output 154 to the operator device 104, which may provide the voice output 156 to the operator 110.

In this example, suppose that the voice output 156 instructs the operator 110 to ignore the loud noise and continue working. In some cases, this instruction sent by the system services 120 may appear to be untrustworthy to the operator 110. Nevertheless, the system 100 may be basing this instruction not only on the voice input 134 received from the operator 110, but also on the sensor data 146 received from the equipment 114, as well as the equipment maintenance records, complaint history for the equipment from this operator and other operators, experience level of the operator 110, and other factors when determining the instruction to provide to the operator 110. Furthermore, if the operator 110 requires more details regarding the instruction, the management program(s) 122 may be configured to provide additional details on the decision-making process applied by the management program(s) 122.

As mentioned above, complaints, observations, and other comments provided by the voice input 134 from the operator 110 are not the only inputs taken into consideration by the system services 120 for determining the possible actions. For example, the management program(s) 122 may obtain information from the equipment sensor data 146, equipment event notifications 148, and external data received from the external system(s) computing device(s) 116. Accordingly, information gathered from a plurality of different data sources may be used by the AI services programs 126 for determining the instruction to provide to the operator 110 for a next course of action. In addition, if the identified problem requires immediate attention, the management program(s) 122 may automatically notify the operator 110 about the nature of the problem and the instructed course of action. Communications between the various data sources, the service computing devices 102, and the operator device 104 may be performed using REST API calls, a data representation format, such as, JSON, and so forth, although implementations herein are not limited to any particular communication format or protocol.

In the system 100, the operator 110 can initiate a system interaction by providing a voice input 134, such as by making an observation, complaint or other comment about the equipment operation, and in response, may receive a voice output 156 providing instructions for course of action. In some cases, the instructions provided by the system may be classified by severity level (for example, high, medium, and low) and instruction type. Severity may be a qualifier for the type of problem being described and may further take into consideration a risk related to continuing to operate the equipment 114. Instruction type may be a high-level classification based on an instruction value that may be continuous or discrete, and may be defined through lookup tables, external data sources, or the like. An example of three instruction types are: "ignore", "quick fix", and "equipment repair". For example, the "quick fix" may be performed by the operator 110 in the field, based on received instructions, while the "equipment repair" might be performed by the technician 112 at a maintenance site.

Further, the combination of a severity level and an instruction type may be used to determine an instruction for an action to be performed by an operator. For example, if the instruction type is "repair" and the severity level is "low", this may indicate that the equipment can continue to be used until the end of the day or other specified time depending on the equipment type and environmental conditions, and the repair may then be performed. Conversely, when instruction type is "repair" and severity level is "high", this may indicate that use of the equipment should stop immediately or as soon as possible for repairs. In addition, because the sensor data 114 may also be streamed or otherwise sent from the equipment 114 in some examples, the management program(s) 122 may independently initiate an instruction as a voice output 156 to the operator 156, such as in the case that the management program(s) 122 detect that the equipment 114 is about to fail based on historical data records and/or real-time sensor data 146, and the like. FIG. 3 discussed below illustrates an example data structure summarizing possible system outcomes in the example described above.

In some cases, the sensor data 146 received by the management program(s) 122 from the equipment 114 may be used to improve overall the accuracy of the instruction sent as the voice output 156 to the operator 110. For instance, typically, the equipment 114, the operator device 104, and the operator 110 are in the field, while the service computing devices 102 and the external system(s) computing device(s) 116 are located in a processing center, data center, etc., somewhere else. Accordingly, the system 100 may be a distributed computing system that supports data analytics processing in the cloud and at the edge as analytics may also be performed on a processor associated with the equipment 114, such as built-in to the equipment 114 or co-located with the equipment 114, before sending the event notification 148 and/or the sensor data 146 to the service computing device(s) 102.

In addition, as still another example, in addition to, or as an alternative to, sending the voice output 156 to the operator 110, the management program(s) 122 may generate one or more control signals 160 and may send the one or more control signals 160 directly to the equipment 114. As one example, suppose that, instead of a vehicle, the equipment 114 is a gas turbine engine for generating auxiliary power, and the sensor data 146 indicates a likelihood that the oil pump is failing, that the severity level is "high", and that the action instruction type is "repair". Accordingly, to prevent further damage to the equipment 114, the management program(s) 122 may send the control signal 160 to the equipment 114 immediately to turn off the equipment 114, and may further send a voice output 156 to the operator 110 to tell the operator 110, using natural language, that the gas turbine is being shut down remotely and the reason for the shutdown. Thus, in some cases, the voice output 156 may be sent to the operator device 104 in reply to receipt of an event notification 148 from the equipment 114 and/or based on analysis of sensor data 146 received from the equipment 114, instead of or in addition to, in reply to a voice input 134 received from the operator 110.

In some cases, as mentioned above, the management program(s) 122 may send an information request 162 to one or more of the external system(s) computing device(s) 116. In response, the external program(s) 118 on the external system(s) computing device(s) 116 may send an information response 164 to the management program(s) 122. The management program(s) 122 may generate the instruction for the operator 110 based at least partially on the received information response 164. As one example, the management program(s) 122 may provide the received information response 164 to the AI services programs 126, along with any voice input 134, equipment history, sensor data 146, etc., as the AI input(s) 142, and may receive the AI output(s) 144 in providing, e.g., an instruction type and/or severity level to enable the management program(s) 122 to determine an instruction to send to the operator device 104, as discussed above. As still another example, the management program(s) 122 may send information about the problem commented on by the operator 110 to the technician device 108 associated with the technician 112. The technician 112 may provide a response to the management program(s) 122, and the management program 112 may provide the response from the technician 112 to the AI services 124 as additional AI inputs 142 when determining a course of action in response to the comment received from the operator 110.

In FIG. 1, the system services 120 may also communicate with the technician device 108 associated with the technician 112. In some examples, the management program(s) 122 may send to the technician device 108 equipment history information 168, which may include all historical information regarding the particular equipment 114, including all the recent exchanges between operator 110 and the management program(s) 122, as well as any sensor data 146 and event notifications 148. In addition, the system services 120 may provide the text, image, video, and/or sound 138 received from the operator device 104, if any. For example, this information 138 and 168 may be sent to the technician device 108 by the time the equipment 114 arrives at the repair site. As mentioned above, this information 138 and 168 may be collected and stored beforehand by the management program(s) 122, such as by receiving this information 138 and 168 from the equipment 114, the operator device 104, the external system computing devices 116, and/or the AI services 124 while the equipment 114 was still in the field. Furthermore, the management program(s) 122 may have already determined and scheduled an optimal technician 112 for working on the equipment 114, such as based on his/her skills. In addition, the management program(s) 122 may have already, ordered parts if needed, and determined and scheduled the optimal repair site to minimize the downtime for the equipment 114.

When the technician begins to work on the equipment 104, the technician may at least initially interact with the system services 120 using one or more technician devices 108. For instance, the technician may use a dedicated client application, may access a web site, or may otherwise communicate with the service computing device(s) 102, such as via a mobile device, tablet computing device, or other computing device, as enumerated elsewhere herein. During this interaction, the management program(s) 122 may instruct the technician to regarding a detailed course of action determined for repairing the equipment. The provided instructions may include a description of components and parts involved as well as actions to be performed in each stage of the repair. In some cases, this information may be sent to the technician device 108 as an audio or text output 170. An example of this information is illustrated in the data structure described below with respect to FIG. 4. The management program(s) 122 may also instruct the technician 112 as to which part of the job to execute first.

During this initial phase, which may be referred to as the diagnosis phase, the technician 112 may receive a voice output 172 from the technician device 108 based on the audio or text output 170 received from the management program(s) 122. Additionally or alternatively, the technician 112 may view text instructions received from the management program(s) 122, and/or may access the equipment history information 168 and/or the text, image, video, and/or sound 138 received from the operator 110.

In addition, the technician 112 may provide a voice input 174, which is sent to the management program(s) 122 by the technician device 108 as speech sound patterns 175 and treated similarly to the speech sound patterns 136 discussed above. In addition to providing the voice input 174, the technician 112 may provide a text input 176 to add additional comments to the equipment history 130, and/or may upload an image, video, and/or sound 178 related to the repairs being performed that may also be stored to one or more of the equipment history data structures 130, thus making this information available to be used in the future by the management program(s) 122 and/or the AI services program 126. In addition, in some cases, the technician device 108 may be used to communicate directly over the one or more networks 106 with one or more of the external system computing devices 116, and/or the AI services 124. In some examples, the interactions between the technician device 108 and the other computing devices, such as the service computing devices 102 and the external system(s) computing devices 116, may be performed using REST API calls and a standard data representation for the exchange of information, such as JSON, or the like.

Following completion of the diagnosis phase, the technician 112 may begin a repair phase. During the repair phase, the technician 112 may communicate with the management program(s) 122 by optionally using a different technician device 108 such as an augmented reality (AR) headset, AR glasses, or the like, to guide the technician step-by-step until the repair is completed accordingly, during this phase, the management program(s) 122 may send AR information 180 to the technician device 108 and/or audio or text output 170 to guide the technician 112 step-by-step during the repair. Alternatively, if augmented reality is not employed, the management program(s) 122 may still send audio output 170 to enable the technician 112 to participate in an interactive voice output 172 and voice input 174 interaction with the management program(s) 122 during the repair. Accordingly, the technician 112 may start and stop the repair process using voice input 174 that may be interpreted by the speech/emotion recognition program 128 included in the system services 120.

In some examples, the management program(s) 122 may receive on-the-fly instructions from the AI services program 126, which may be forwarded to the technician 112 and/or may retrieve 3-D models, such as from the external systems computing devices 116, which may be sent to the technician 112 at each step of the repair process. The management program(s) 122 may reply to the technician 112 via voice outputs 172 regarding what to do next and, in the case that augmented reality is employed, by superimposing 3D models, computer-generated video, and/or text with instructions onto the real objects that are being repaired concern.

Upon completion of each successive step of the repair process, the technician may provide a voice input 174, such as "step completed, next action" and the management program(s) 122 may retrieve information related to the next action for the current repair process. This interactive process between the technician and the management program(s) 122 may be repeated until the repair is completed and the system informs the technician 112 such as with a voice output 172, e.g., "repair completed, no further action required". In above-described the method, the management program(s) 122 are able to interact with a technician 112 by guiding the technician 112 through the repair process, thereby improving productivity by reducing repair time for non-experienced technicians 112 and even experienced technicians 112. In addition, the implementations herein may increase the efficiency of performing repairs, such as by enabling a technician 112 to work on repair tasks even without prior training, as well as providing training to junior technicians 112, thereby fast tracking their skills and proficiency for making repairs.

The system 100 herein is able to provide a rich human-computer interaction that integrates a distributed network of user devices, sensors, AI and machine learning in a natural way through voice communication using speech patterns that enhance AI usability and human trust in AI outputs. The speech recognition capability herein enables translation of spoken language into text by the service computing device(s) 102, sometimes referred to as speech-to-text.

Using the text produced by the speech recognition techniques discussed additionally below, the service computing device(s) 102 can interact with users through voice communication as the main user interface for the system 100.

The system 100 may use the speech and/or emotion recognition program 128 to recognize sound waves as speech and convert the speech to text. For example, when the management program(s) 122 receive the speech sound patterns 136, the management program(s) 122 may invoke the speech and/or emotion recognition program 128, which convert the received speech to text. Any conventional speech-to-text conversion program may be used in some implementations herein. In addition, the speech and/or emotion recognition program 128 may extract relevant features from the received speech sound patterns 136 for determining the tone, attitude, or other emotions underlying the received speech sound patterns. Some examples of the extracted features may include, but are not limited to: pitch, tone, accent, emphasis, pronunciation, volume, articulation, nasality, speed, timbre, etc. These extracted sound features may then be used as an input to an emotion-recognition machine learning model configured for performing emotion recognition (which may be one of the MLM(s) and associated programs 132 in some examples) to provide an indication of an emotional state of the person speaking which may be used to enhance the audio or text output 154, such as the instructions, suggestions, recommendations, or the like.

Accordingly, examples herein may combine conventional speech-to-text techniques with emotional interpretation to produce a more accurate response to the operators or technicians using the system 100. This may add another dimension to solving the problem of computer understanding of human voice commands by not only using the text translated from speech, but by also taking into consideration metadata extracted from voice waves. The system 100 may enrich human-computer interactions by providing additional information related to emotions, sense of urgency, or the like, that can be considered for making accurate decisions in an enterprise or industrial scenario with short conversations. Furthermore, implementations herein differ from conventional emotion analysis and natural language understanding approaches that are typically employed on blogs, social media, social networks, review materials, healthcare documents, survey responses, and microblogs such Twitter, as the implementations herein do not rely on user-generated text as the input.

Some examples herein may include an initial training stage prior to use the speech and/or emotion recognition program 128 to recognize speech patterns and associated emotions. For instance, the speech and/or emotion recognition program 128 may first train an emotion recognition MLM for each person, i.e., each operator and each technician. Following training of a respective model for each operator and technician, the system may identify the individual providing the voice input, and may access the trained MLM trained for that individual to enable the system to recognize the speech and emotions in real time and act accordingly.

Training may be performed by providing the individual with a list of phrases and by asking the individual to speak the phrases in a normal manner and a non-normal manner. For example, during training, the system may send or may otherwise provide a plurality of phrases, such as a plurality of sentences, to the user. After the samples for training are received, the sound features may be extracted and a model may be trained on the system for the particular operator or technician based on the received phrases. An entry to the model can be expressed as a pair $E_i=<stt_i, sf_i>$ where $su_i$ represents the speech-to-text entry $E_i$ and $sf_i$, represents the expected sound features of the speech-to-text entry $E_i$. For instance, suppose there are n patterns to be extracted from a sound wave, then $sf_i$ can be further decomposed as $sf_i=\{p_{i1}, p_{i2}, \ldots, pin\}$. Each entry $E_i$ is classified to a label $L_i$ that is normal or non-normal. Non-normal patterns may be further classified into emotion categories such as angry, anxious, stressed, nervous, urgent, etc.

Therefore, the system 100 may consider, in real-time, speech and other information received from an operator or technician as an input for determining an instruction, recommendation, or other response to make to the operator or technician. For example, a normal voice pattern (i.e., with no uncharacteristic emotion) may be treated a not affecting the response generated by the management program(s) 122 as the output to the operator or technician. On the other hand, when a non-normal emotion is detected, such as anxiousness or anger, the proposed response may be changed, depending upon comments made by the operator or technician.

As one example, consider a situation in which an operator 110 is working on the equipment 114, and makes a comment, such as an observation or complaint. The system 100 may provide an instruction for repair based on the voice input received from the operation, which may be based on detecting a non-normal emotional pattern in the operator's voice, such as that the operator 110 is angry or frustrated. Based on this determination, the system services 120 may initiate a repair site procedure by scheduling maintenance for the equipment at the repair site automatically and by following different actions that may be taken. For instance, based on detecting the anger or frustration, the management program(s) 122 may send a request to assign a higher skill level or senior technician instead of a junior technician for this repair, particularly if the complaint/observation is a repeated problem that was already supposed to have been corrected. As another example, the management program(s) 122 may immediately put the operator 110 into direct contact with an appropriate technician, such as through a telephone or other a communication device. As another example, the management program(s) 122 may provide a detailed explanation of the problem and/or operational guidance of managing the equipment in each communication with the operator 110 while continuing to monitoring the emotions detected in the operator's speech pattern. This step-by-step guidance and support provided to the operator of the equipment may be stopped when the operator's speech pattern becomes normal, i.e., the anger or frustration is no longer detected.

In some cases, the management program(s) 122 may take into consideration a plurality of parameters, which may include, but are not limited to, repetition or recurrent repair, parts availability, equipment downtime, operator distress (emotions indicated by voice pattern), the number of operator complaints received about the problem, the skills of available technicians, ability to solve the issue, and the like. Thus, the management program(s) 122 may schedule a repair date and time with priority in an optimal way. This may include rescheduling of a previously scheduled equipment repair and may include communications with the external systems computing devices 116, such as for determining parts availability, technician availability, repair site availability, and so forth.

As mentioned above, the management program(s) 122 programs may store received data in the one or more equipment history data structures 130. An example of data that the system 100 may receive includes equipment attributes, which may include structured data that encode the attributes of the equipment 114 subject to repair. Examples of equipment attributes include, but are not limited to, the make and model of the equipment, the manufacturing year, and the capacity and ratings of the equipment and its components. For the same symptoms, different types of equipment might require different repair actions. Therefore, equipment attributes may be used during the building and training of machine learning models to train the models to determine the correct repair for each equipment type when provided with the symptoms of the problem.

As another example, the equipment history data structure(s) 130 may store equipment usage data, which may be structured data related to the usage of the equipment over the life of the equipment since the start of operation of the equipment. Examples include age, operating hours, mileage, payloads, and so forth. Usage data be used for determining the correct repair actions given the symptoms of the problem that needs to be fixed.

As another example, the equipment history data structure(s) 130 may store sensor data received from the equipment. For example, the sensor data may be time series data collected from various sensors before the equipment was sent for repair. Each time series may represent the readings of the corresponding sensor over time. Further, each sensor reading may be associated with a timestamp that specifies the date and time of the reading.

Further, the equipment history data structure(s) 130 may store event data, such as based on event notifications, error messages, or the like, received from the equipment before the equipment failed or was sent for repair. The events may be of different types, and may include maintenance actions, as well as alerts or other notifications, error messages received from the equipment, and error messages received from other systems in the environment of the equipment. Each of the events may be associated with a timestamp that specifies the date and time of the event occurrence.

In addition, the equipment history data structure(s) 130 may store user complaints, observations, and other types of comments made by the user with respect to the equipment. These may be natural language comments about the equipment made by user, such as via the operator device. These unstructured or semi-structured data may describe the symptoms of the problem to be fixed (e.g., "loud noise from the back of the equipment). User comments may be received before or during the repair process, and may be received in various different formats including, but not limited to, voice inputs, typed text, handwritten text, and so forth.

Additionally, the equipment history data structure(s) 130 may store other complaint-related data, which may include additional information about the problem to be fixed. Examples of other complaint-related data may include images of defective parts, sound files from recordings made by the user, videos of the defective parts, images of the equipment, and so forth. These other data may be submitted to the system before or during the repair process.

In addition, the equipment history data structure(s) 130 may store repair history of each equipment managed by the system 100. The repair history may include a record of historical repairs that have been performed on the equipment to fix previous problems with the equipment. Each repair action may be associated with a timestamp that specifies the date and time of the repair. The stored repair action record may also include attributes that describe different aspects of the repair such as the system(s) and subsystem(s) in which the problem occurred, the component(s) to be repaired, the part(s) associated with the repair, and the action(s) performed during the repair (e.g., clean, inspect, replace, etc.).

In addition, the equipment history data structure(s) 130 may store metadata and additional information. The metadata and additional information may describe extra information that may be used to enrich the overall system knowledge about the equipment and repairs, such as, the environment in which the equipment 114 is operated, repair shop components and parts availability, technician skills at each repair site, and the like. This may include, but is not limited to, the operation conditions (e.g., operation hours), environment conditions (e.g., location, temperature, humidity, dust), and maintenance records (e.g., date, conditions, notes). All these data may be received and stored in structured, semi-structured, or unstructured formats and, in some cases, may be acquired from the external systems.

Additionally, the system 100 may output data in several different types and formats. For example, the instructions to the operator or technician may be natural language or structured instructions, such as text, provided by the system 100 to the operator or technician. The instructions may be triggered by the equipment, the operator, the technician, or the system itself, such as in the case of analyzing received sensor data as input and taking into consideration additional data, such as repair history, OEM specifications, equipment attribute data and metadata. The instructions may be output in different formats including but not limited to voice, text, augmented reality (AR), 2D or 3D images, and videos (AR or not), and so forth. The instructions may take into consideration the environment of use, the equipment condition and history, operator and technician skills, operator and technician voice patterns and comments, and so forth.

Additionally, the system may provide alerts to the operators or technicians in some situations, such as in the case of failure prediction events. The system 100 may trigger these alerts based on the data such as sensor data, event notification data, and metadata information. The alerts may be provided in various formats, such as natural language via the client application, voice message, or telephone call, SMS text message, website pop-up, sounds emitted by devices, mobile notifications, page alerts, and the like.

In addition, as mentioned above, in some cases, the system may use one or more control signals to directly remotely control the equipment, such as to prevent damage to the equipment, the operator, other people, other property, or the like. The control signal may be sent directly to the equipment, and, for example, may shut down the equipment or may merely change a setting of the equipment. The control signal may be triggered based on one more of sensor data, event notification data, metadata information, operator comments, or the like. Typically, the sending of a control signal may be performed contemporaneously with the sending of an instruction or alert to the operator 110, such as to inform the operator 110 that the equipment is being remotely controlled, and the reason therefor.

Further, while several examples are discussed above, numerous other variations will be apparent to those of skill in the art having the benefit of the disclosure herein. The system 100 herein enables use of AI and machine learning techniques for equipment management and maintenance using voice interactions. Accordingly, the operator 110 may provide voice data inputs (e.g., voice signals and speech-to-text) while using the equipment 114 in the field. Further, a technician at the repair site may similarly provide natural language voice inputs as an input to the system 100. Additionally, the system may provide real-time feedback and easy to understand instructions for an operator in the field using AI and machine learning techniques. In addition, the system 100 provides information integration between the external systems, in-the-field data, and maintenance repair site operations, thereby enabling a seamless end-to-end experience for the operator 110. In addition, in some cases, the system 100 may provide detailed step-by-step instructions based on AI and machine learning to the technician 112, who may then use this information to perform repairs. For example, the management program may provide this information as a natural language voice to the technician 112. Accordingly, both the operator 110 and the technician 112 are able to communicate with the system 100 in real time using natural language speech, rather than having to use text or other communication techniques. Furthermore, because voice is used as the primary input and output techniques for the system, the operator 110 and the technician 112 may communicate with the system in a hands-free manner, which may be useful in a number of situations such as on the road, at the repair site, etc.

Figure 2:
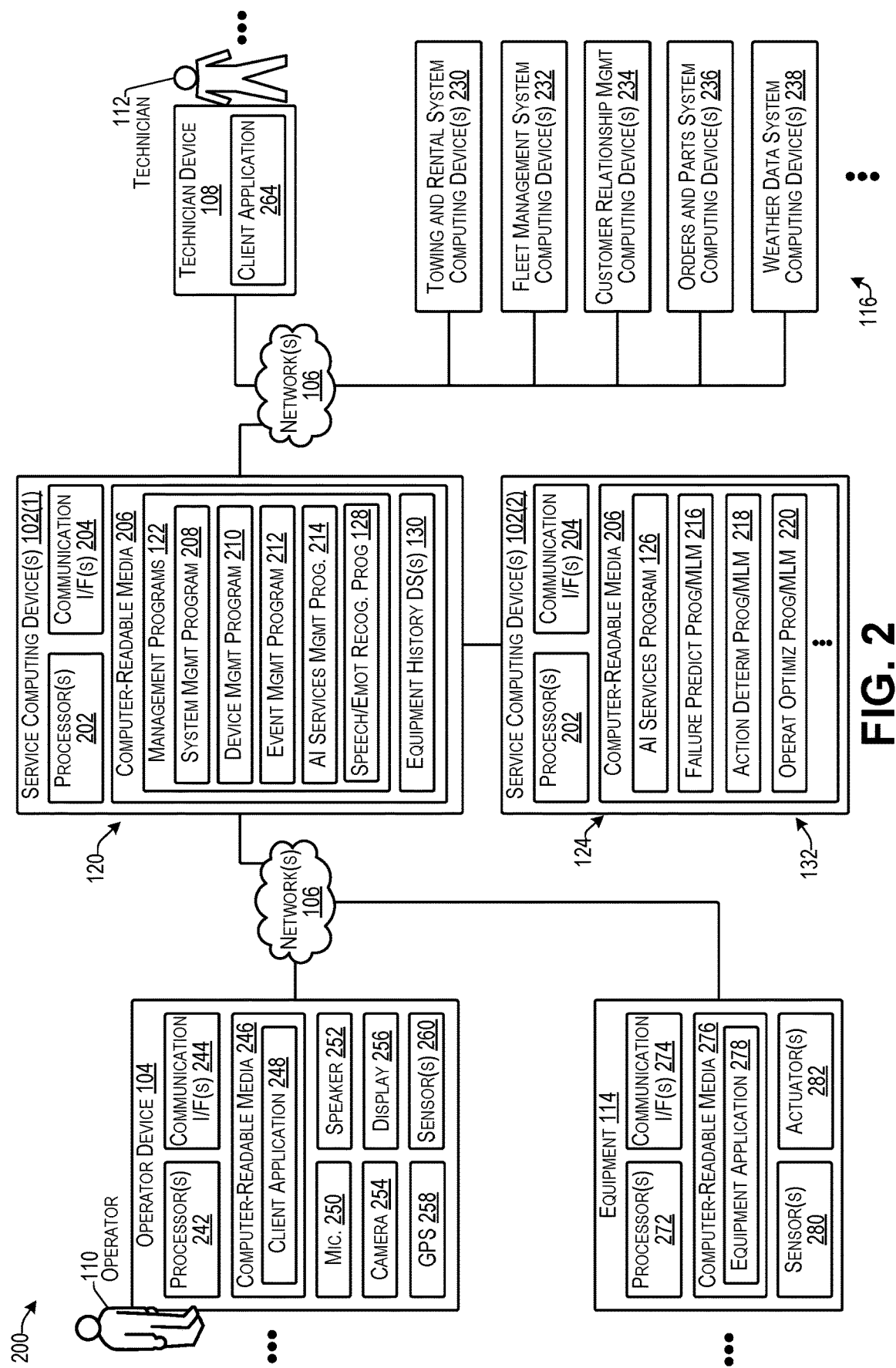
FIG. 2 illustrates an example system architecture for equipment management and maintenance according to some implementations.

FIG. 2 illustrates an example system architecture 200 for equipment management and maintenance according to some implementations. In some examples, the system architecture 200 may correspond to the system 100 discussed above. In some implementations, the service computing device(s) 102 may include one or more servers, personal computers, or other types of computing devices that may be embodied in any number of ways. For instance, in the case of a server, the programs, other functional components, and at least a portion of data storage may be implemented on at least one server, such as in a cluster of servers, a server farm or data center, a cloud-hosted computing service, and so forth, although other computer architectures may additionally or alternatively be used.

In the illustrated example, the service computing device 102 may include, or may otherwise have associated therewith, one or more processors 202, one or more communication interfaces 204, and one or more computer-readable media 206. Each processor 202 may be a single processing unit or a number of processing units, and may include single or multiple computing units, or multiple processing cores. The processor(s) 202 may be implemented as one or more central processing units, microprocessors, microcomputers, microcontrollers, digital signal processors, state machines, logic circuitries, and/or any devices that manipulate signals based on operational instructions. For instance, the processor(s) 202 may be one or more hardware processors and/or logic circuits of any suitable type specifically programmed or configured to execute the algorithms and processes described herein. The processor(s) 202 may be configured to fetch and execute computer-readable instructions stored in the computer-readable media 206, which can program the processor(s) 202 to perform the functions described herein.

The computer-readable media 206 may include volatile and nonvolatile memory and/or removable and non-removable media implemented in any type of technology for storage of information such as computer-readable instructions, data structures, program modules, or other data. For example, the computer-readable media 206 may include, but is not limited to, RAM, ROM, EEPROM, flash memory or other memory technology, optical storage, solid state storage, magnetic tape, magnetic disk storage, RAID storage systems, object storage systems, storage arrays, network attached storage, storage area networks, cloud storage, or any other medium that can be used to store the desired information and that can be accessed by a computing device. Depending on the configuration of the service computing device 102, the computer-readable media 206 may be a tangible non-transitory medium to the extent that, when mentioned, non-transitory computer-readable media exclude media such as energy, carrier signals, electromagnetic waves, and/or signals per se. In some cases, the computer-readable media 206 may be at the same location as the service computing device 102, while in other examples, the computer-readable media 206 may be partially remote from the service computing device 102.

The computer-readable media 206 may be used to store any number of functional components that are executable by the processor(s) 202. In many implementations, these functional components comprise executable instructions and/or programs that are executable by the processor(s) 202 and that, when executed, specifically program the processor(s) 202 to perform the actions attributed herein to the service computing device 102. Functional components stored in the computer-readable media 206 of the first service computing device(s) 102(1) may include the management program(s) 122. The management program(s) 122 may include one or more computer programs, computer-readable instructions, executable code, or portions thereof that are executable to cause the processor(s) 202 to perform various tasks as described herein. In the illustrated example, the management program(s) 122 may include or may access a system management program 208, a device management program 210, an event management program 212, and an AI services management program 214. In addition, the computer-readable media 206 may include the speech and/or emotion recognition program 128 as discussed above, and as discussed additionally below, e.g., with respect to FIG. 14.

Each of these functional components 208-214 may be an executable program module of the management program(s) 122, or a portion thereof. Alternatively, in other examples, some or all of these components 208-214 may be separately executable standalone computer programs that may be invoked by the management program(s) 122. For example, the system management program 208 may configure the one or more processors 202 to perform overall management of the system services according to the examples herein, such as discussed above with respect to FIG. 1. Furthermore, the device management program 210 may manage interactions with the operator devices 104 and the technician devices 112, such as for sending and receiving information in any of various formats, including voice, text, images, video, sound, augmented reality, and so forth. Furthermore, the event management program 212 may manage interactions with the equipment 114, such as for receiving sensor data and/or event notifications, and for sending acknowledgements and/or control signals to the equipment 114. In addition, the AI services management program 214 may manage communications with the AI services program 126, such as for sending AI inputs to the AI services program 126, and for receiving AI outputs from the AI services program 126.

In addition, the second service computing device(s) 102(2) may include the processor 202, communication interfaces 204, and computer readable media 206 similar to that discussed above with respect to the first service computing device(s) 102(1). However, the second service computing device(s) 102(2) may include different functional components such as the AI services program 126, a failure prediction program and/or MLM 216, an action determining program and/or MLM 218, and an operating optimizing program and/or MLM 220. Various versions of the MLM 216, 218, and 220 are known in the art. For example, International PCT Application No. PCT/US17/55461, filed Oct. 6, 2017, entitled REPAIR MANAGEMENT AND EXECUTION, incorporated by reference herein, and assigned to the same assignee as herein describes MLMs and associated programs for providing repair instructions, maintenance recommendations, and the like, that may be employed by the AI services 124 according to some examples herein. Furthermore, while several types of machine learning models and associated programs for training and executing the respective machine learning models are illustrated in this example, additional or alternative types of machine learning models and associated programs may be included in other examples, as will be apparent to those of skill in the art having the benefit of the disclosure herein.

Additionally, the functional components in the computer-readable media 206 may include an operating system (not shown in FIG. 2) that may control and manage various functions of the respective service computing device(s) 102. In some cases, the functional components may be stored in a storage portion of the computer-readable media 206, loaded into a local memory portion of the computer-readable media 206, and executed by the one or more processors 202. Numerous other software and/or hardware configurations will be apparent to those of skill in the art having the benefit of the disclosure herein.

In addition, the computer-readable media 206 may store data and data structures used for performing the functions and services described herein. For example, the computer-readable media 206 may store the equipment history data structures 130 that may be used by the programs herein, such as the management program(s) 122 and the AI services program 126. In addition, in some cases, the equipment history data structures 130 may be used as training data for training the machine learning models 216, 218 and/or 220. Examples of the machine learning model(s) 216, 218 and/or 220 may include classification models such as random forest, support vector machines, or deep learning networks. Additional examples of the machine learning models 140 may include predictive models, decision trees, regression models, such as linear regression models, stochastic models, such as Markov models and hidden Markov models, artificial neural networks, such as recurrent neural networks, and so forth. Accordingly, implementations herein are not limited to a particular type of machine learning model.

The service computing device(s) 102 may also include or maintain other functional components, data and data structures, which may include programs, drivers, etc., and the data and data structures used or generated by the functional components, as discussed additionally below. Further, the service computing device(s) 102 may include many other logical, programmatic, and physical components, of which those described above are merely examples that are related to the discussion herein.

The communication interface(s) 204 may include one or more interfaces and hardware components for enabling communication with various other devices, such as over the one or more networks 106. Thus, the communication interfaces 204 may include, or may couple to, one or more ports that provide connection to the network(s) 106 for communicating with other service computing devices 102, the operator devices 104, the technician devices 108, the equipment 114, and/or one or more external computing devices 116. For example, the communication interface(s) 204 may enable communication through one or more of a LAN (local area network), WAN (wide area network), the Internet, cable networks, cellular networks, wireless networks (e.g., Wi-Fi) and wired networks (e.g., fiber optic, Ethernet, Fibre Channel), direct connections, as well as short-range wireless communications, such as BLUETOOTH®, and the like, as additionally enumerated elsewhere herein.

Further, the external computing devices 116 may include configurations and hardware similar to those discussed above with respect to the service computing device(s) 102, but with different functional components, such as the external programs and different data. In some examples herein, one or more computing devices may be employed by each separate external system. Examples of external systems and corresponding computing devices illustrated in FIG. 2 include towing and rental system computing device(s) 230, fleet management system computing device(s) 232, customer relationship management computing device(s) 234, orders and parts system computing device(s) 236, weather data system computing device(s) 238, and so forth.

In some examples, the operator device 110 may be any type of computing device able to communicate over a network including smart phone computing devices, tablet computing devices, wearable computing devices, augmented reality computing devices, desktop computing devices, laptop computing devices, embedded computing devices, such as electronic control units, and so forth. In the case that the operator device is such a computing device, the operator device 104 may include one or more processors 240, one or more communication interfaces 242 and one or more computer-readable media 244. For example, the processor(s) 240 may be any of the processor(s) 202 discussed above with respect to the service computing device(s) 102, the communication interfaces 244 may be any of the communication interfaces 204 discussed above with respect to the service computing device(s) 102, and the computer-readable media 246 may be any of the computer-readable media 206 discussed above with respect to the service computing device 102.

The computer readable media 246 may include a client application 248 stored thereon executable by the one or more processors 242 for performing the functions described above of the operator device 104. In addition, in some examples, the operator device may include various additional components such as a microphone 250, a speaker 252, a camera 254, a display 256, a GPS receiver 258, and one or more sensors 260. Example of the sensors 260 may include an accelerometer, gyroscope, compass, a proximity sensor or any of various other sensors known to those of skill in the art. Furthermore, while the operator device 104 is illustrated in this example as being a computing device including a processor and executable code, in other examples, the operator device may include a microphone and speaker, such as an in the case of an intercom or the like.

The technician device 108 may have a hardware configuration similar to that discussed above for the operator device 104, or in some examples, may be different, such as in the case of augmented reality goggles, or the like. The technician device 108 may include a client application 264, which may be the same as or similar to the client application 248, or which may be different therefrom for enabling the different functions performed by the technician 112, e.g., as discussed above with respect to FIG. 1. Further, in some cases, the client application 264 may be a browser for accessing a website provided by the system services herein.

The equipment 114 may include or may have associated therewith one or more processors 272, one or more communication interfaces 274, and one or more computer readable media 276. For example, the processor(s) 240 may be any of the processor(s) 202 discussed above with respect to the service computing device(s) 102, the communication interfaces 244 may be any of the communication interfaces 204 discussed above with respect to the service computing device(s) 102, and the computer-readable media 246 may be any of the computer-readable media 206 discussed above with respect to the service computing device 102. Additionally, for some types of equipment, such as vehicles, the one or more processors 272 may include one or more electronic control units or other types of embedded processors included in the equipment 114.

The computer readable media 276 may include one or more functional components such as an equipment application 278 which may be executed by the one or more processors 272 for performing the functions of the equipment 114 discussed above, e.g., with respect to FIG. 1. In some cases, the equipment application 278 may be or may include firmware for forwarding sensor data from the one or more sensors 280. In other cases, the equipment application 278 may include an analysis function such as for analyzing the sensor data received from the sensors 280. In some cases, the equipment application 278 may perform image processing of the sensor data and may send an event notification to the service computing devices 102 in the case that the equipment application 278 detects an anomaly, failure, or other problem with the equipment 114.

In addition, the equipment 114 may include one or more actuators 282. For example, the one or more actuators 282 may be activated remotely by one or more control signals such as for controlling at least a portion of the equipment 114. As mentioned above, in some cases and for some types of equipment 114, the management program(s) 122 may send a control signal to the one or actuators 282, such as for shutting down the equipment 114 or otherwise controlling one or more functions of the equipment 114, such as in the event that repair is required and the severity level is high, or the like.

The system services 120 may employ one or more APIs for communication with the AI services 124, the devices 104 and 108, the equipment 114, and the external systems computing devices 116. The REST API is described as one example of an API according to some implementations herein; however, the implementations herein are not limited to any particular APIs, communication protocols, communication formats, or the like.

When equipment 114, an operator device 104 used by an operator 110, or a technician device 108 used by a technician 112 sends a communication to the management programs 122, the system management program 208 may receive the communication and at least one of analyze, dispatch, store, or coordinates communications between other programs, computing devices and services. For example, the system management program 208 may act as a hub that integrates the entire system 200, such as by connecting equipment 114, operator devices 104, technician devices 108, external system computing devices 116, and the AI services 124 in real-time for ensuring correct task executions.

As one example, when a request or other input is received by the system services 120, the system management program 208 may coordinate an execution as follows: a) process the information; b) send a request to one or more of the external computing devices 116 if additional information available from the one or more external computing devices 116 is required; d) store relevant information, such as in the equipment history data structures 130 or other suitable data structures; e) the system management program 208 may send pertinent information to the AI services management program 214; f) the AI services management program 214 may process the received information and send the received information to the AI services program 126, which may invoke the appropriate MLM, or the like; g) the AI services program 126 may return an AI output to the AI services management program 214, which forwards the AI output to the system management program 208; h) the AI services management program 214 or the system management program 208 may store the AI output in the one or more equipment history data structures 130 in association with the equipment in question; i) the system management program 208 may generate a response based at least partially on the AI output 144, and may send the response as one or more electronic communications to the appropriate device(s) and/or equipment(s).

Accordingly, the examples herein provide a distributed computing system that uses AI and machine learning for equipment management and maintenance using voice interactions. The voice data input may be received from an operator in natural language while the operator is using the equipment in the field. The system 200 may provide realtime voice feedback instructions in the field to the operator using natural language tailored for clear and easy understanding. The instructions may be tailored to the operator considering the environment of use, the equipment condition and history, skills of the operator, comments made by the operator, and any detected emotions indicated by the operator.

Furthermore, the system may compose and send detailed instructions to a technician, which may include identifying a component to be repaired, a part or tool to be used, and/or action to be performed to repair the equipment, while considering skills and any comments received from the technician. The system may provide step-by-step instructions to the technician at the repair site, which may employ combinations of AI and machine learning, voice instructions, and AR outputs to improve the repair time and technician productivity. The system may integrate data received from various sources such as the external systems, sensor data from the equipment, data received from the operator in the field, and provide this data to the maintenance repair site for use by a technician, thereby enabling a seamless end-to-end experience. Thus, the system enables users to provide comments regarding the equipment in a hands-free manner by using voice as the input and output of an AI system. Consequently, implementations herein improve system usability, improve user engagement, and improve user confidence in the AI System through the use of voice communications in a manner similar to the way humans interact with each other.

Additional description of the system services 120 are discussed below with respect to FIGS. 11-14. Furthermore, the data structures of FIGS. 5-10 discussed below set forth examples of data and schema snippets that may be obtained by the system management program 208 from the external systems computing devices 116 to enable the system management program 208 to gather information to enrich its operation.

FIG. 3 illustrates an example data structure 300 showing an action instruction summary according to some implementations. For instance, the data structure 300 may indicate the possible system outcomes for some examples of the system 100 herein, e.g., as discussed above with respect to FIG. 1. The data structure 300 in this example includes an initiator 302, an input type 304, an output type 306, a severity level 308, and an action instruction type 310.

In the case that the initiator 302 is the operator, as indicated at 312, the input type 304 may be a comment, such as an observation, complaint, or report; the output type 306 may be easy-to-understand natural language instruction by voice provided to the operator; the severity level 308 may be one of high, medium, or low; and the action instruction type 310 may be ignore, quick fix, or repair. Furthermore, in the case that the initiator 302 is the equipment, as indicated at 314, the input type 304 may be sensor data and/or an event notification; the output type 306 may be easy-to-understand natural language instruction by voice to the operator and/or a control signal to the equipment; the severity level 308 may be one of high, medium, or low; and the action instruction type 310 may be one of ignore, quick fix, or repair.

FIG. 4 illustrates an example data structure 400 including a detailed action instruction for a technician according to some implementations. For instance, as discussed above with respect to FIG. 1, the data structure 400 may include an indication of an event, such as an equipment failure or other equipment problem. The data structure 400 may further include an identification of the component 404, such as a system in which the event has been detected, along with a confidence level percentage 406 that the identified component is correct. The data structure 400 may further include an indication of the part 408, such as the part that is predicted to have failed or otherwise is in need of repair, along with a confidence level percentage 410 that indicating the level of confidence that the identified part is correctly identified as the problem. In addition, the data structure 400 may include an action type 412 along with a confidence level 414 indicating the level of confidence that the selected action is the correct action for addressing this problem.

In the illustrated example, a first event 402 may be a water pump leak, as indicated at 416, and the system is 100 percent confident that the leak is coming from the cooling system. The system is further 100 percent confident that the part is the water pump assembly, and the system is 95 percent confident that the correct action is to replace the water pump assembly. Similarly, a second event is an engine noise, as indicated at 418, in which the component is included in a power plant system with 100 percent confidence, and the system is 90 percent confident that the part is included in the engine assembly parts. In addition, the system is 85 percent confident that the correct action is to diagnose the cause of the engine noise.

FIG. 5 illustrates an example data structure 500 showing fleet management data for equipment identifier (ID) according to some implementations. In this example, the data structure 500 includes equipment sample data and a schema snippet from a fleet management external system for identifying equipment. In the illustrated example, the data structure 500 includes an equipment ID 502, a make 504, a model, 506, a year 508, an indication of whether or not the equipment is leased 510, mileage 512, engine size 514, and so forth. Accordingly, the data structure 500 may be used by the system services for identifying various attributes of a particular equipment corresponding to the equipment ID 502.

FIG. 6 illustrates an example data structure 600 including customer relationship management data for an operator according to some implementations. In this example, the data structure 600 includes operator sample data and a schema snippet from a customer relationship management external system. In the illustrated example, the data structure 600 includes an operator ID 602, a first name 604, a last name 606, a license number 608, and experience level 610. Accordingly, the data structure 600 may be used by the system services for determining various information about a particular operator corresponding to the operator ID 502.

FIG. 7 illustrates an example data structure 700 showing repair site fleet management data according to some implementations. In this example, the data structure 700 includes repair site sample data and a schema snippet from a fleet management external system for repair sites. In the illustrated example, the data structure 700 includes a repair site identifier 702, a repair site name 704, a repair site city 706, a repair site GPS latitude 708, and a repair site GPS longitude 710. Accordingly, the data structure 700 may be used by the system services for determining various information about a particular repair site corresponding to the repair site ID 702.

Figure 8:
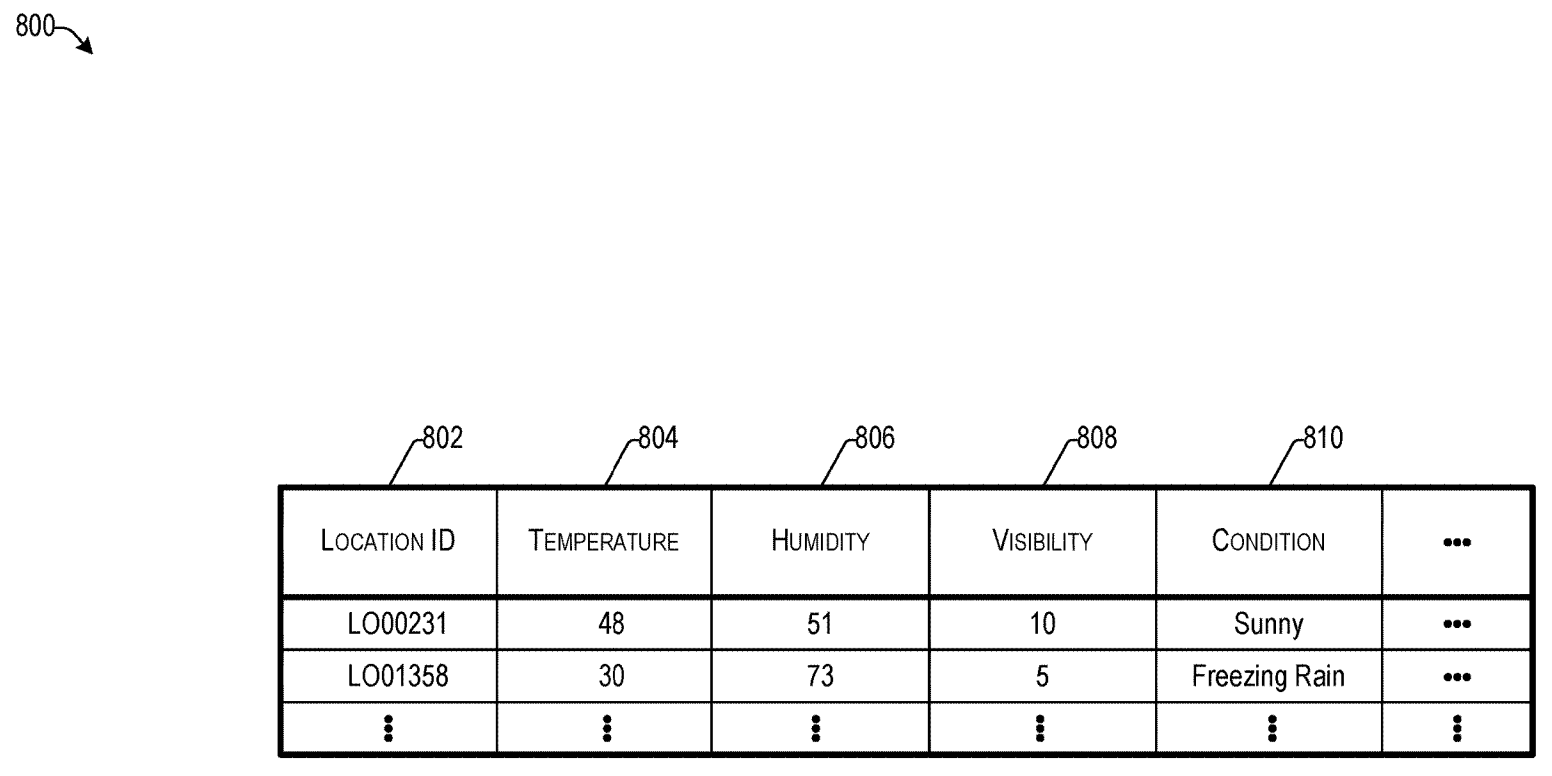

FIG. 8 illustrates an example data structure 800 showing weather sample data according to some implementations. In this example, the data structure 800 includes weather sample data and a schema snippet from a weather data external system. In the illustrated example, the data structure 800 includes a location ID 802, a temperature 804, a humidity 806, a visibility 808, and a condition 810. Accordingly, the data structure 800 may be used by the system services for determining various information about the weather at a particular location corresponding to the location ID 802.

FIG. 9 illustrates an example data structure 900 showing parts data according to some implementations. In this example, the data structure 900 includes parts sample data and a schema snippet from an order and parts external system. In the illustrated example, the data structure 900 includes a part ID 902, a part name 904, a part supplier 906, a part description 908, a component/assembly 910 corresponding to the part, and an inventory 912 of the part. Accordingly, the data structure 900 may be used by the system services for determining various information about a selected part, as indicated by the corresponding part ID 902.

FIG. 10 illustrates an example data structure 1000 showing technician information according to some implementations. In this example, the data structure 1000 includes technician sample data and a schema snippet from a fleet management external system. In the illustrated example, the data structure 1000 includes a technician ID 1002, a first name 1004, a last name 1006, a skill level 1008, a specialist identification 1010, and a list of skills 1012. Accordingly, the system services may use the data structure 1000 to determine information about a technician corresponding to the technician ID 1002.

FIGS. 11-14 are flow diagrams illustrating example processes according to some implementations. The processes are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the processes are described with reference to the environments, frameworks, and systems described in the examples herein, although the processes may be implemented in a wide variety of other environments, frameworks, and systems.

Figure 11:
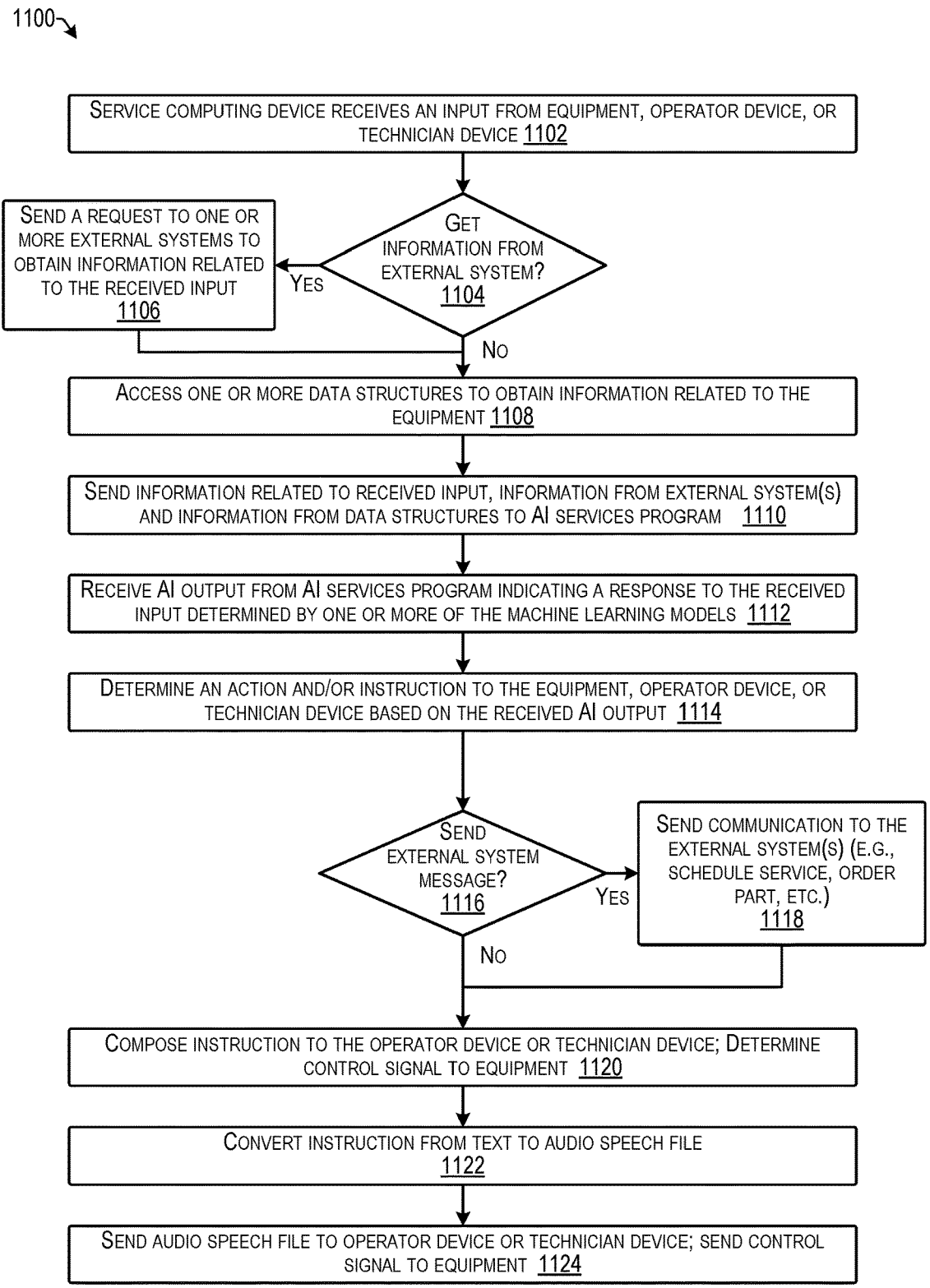
FIG. 11 is a flow diagram illustrating an example process for receiving a voice input from a device and providing an audio speech output in reply according to some implementations.

FIG. 11 is a flow diagram illustrating an example process 1100 for receiving a voice input from a device and providing an audio speech output in reply according to some implementations. In some examples, the process 1100 may be performed by one or more processors of the service computing device 102 by executing the management program(s) 122 for performing at least some of the operations described in the process 1100.

At 1102, the computing device may receive an input from the equipment, the operator device, or the technician device.

At 1104, the computing device may determine whether to get information from one or more of the external systems computing devices. If so, the process goes to 1106. If not, the process goes to 1108.

At 1106, the computing device may send a request to one or more external systems to obtain information related to the received input.

At 1108, the computing device may access one or more data structures to obtain information related to the equipment.

At 1110, the computing device may send information related to the received input, information from external system(s), and information from data structures to the AI services program.

At 1112, the computing device may receive the AI output from the AI services program indicating a response to the received input, as determined at least partially by one or more of the machine learning models.

At 1114, the computing device may determine an action and/or instruction to the equipment, operator device, or technician device based on the received AI output.

At 1116, the computing device may determine whether to send an external system message based on the received AI output. If so, the process goes to 1118. If not, the process may go to 1120.

At 1118, the computing device may send communication to the external subcomponent (e.g., schedule service, order part, etc.).

At 1120, the computing device may compose an instruction to the operator device or the technician device. Additionally, or alternatively, in some cases, the computing device may determine a control signal to send to the equipment.

At 1122, the computing device may convert the instruction from text to and audio speech file.

At 1124, the computing device may send the audio speech file to the operator device or technician device. Additionally, or alternatively, in some examples the computing device may send a control signal to the equipment.

Figure 12:
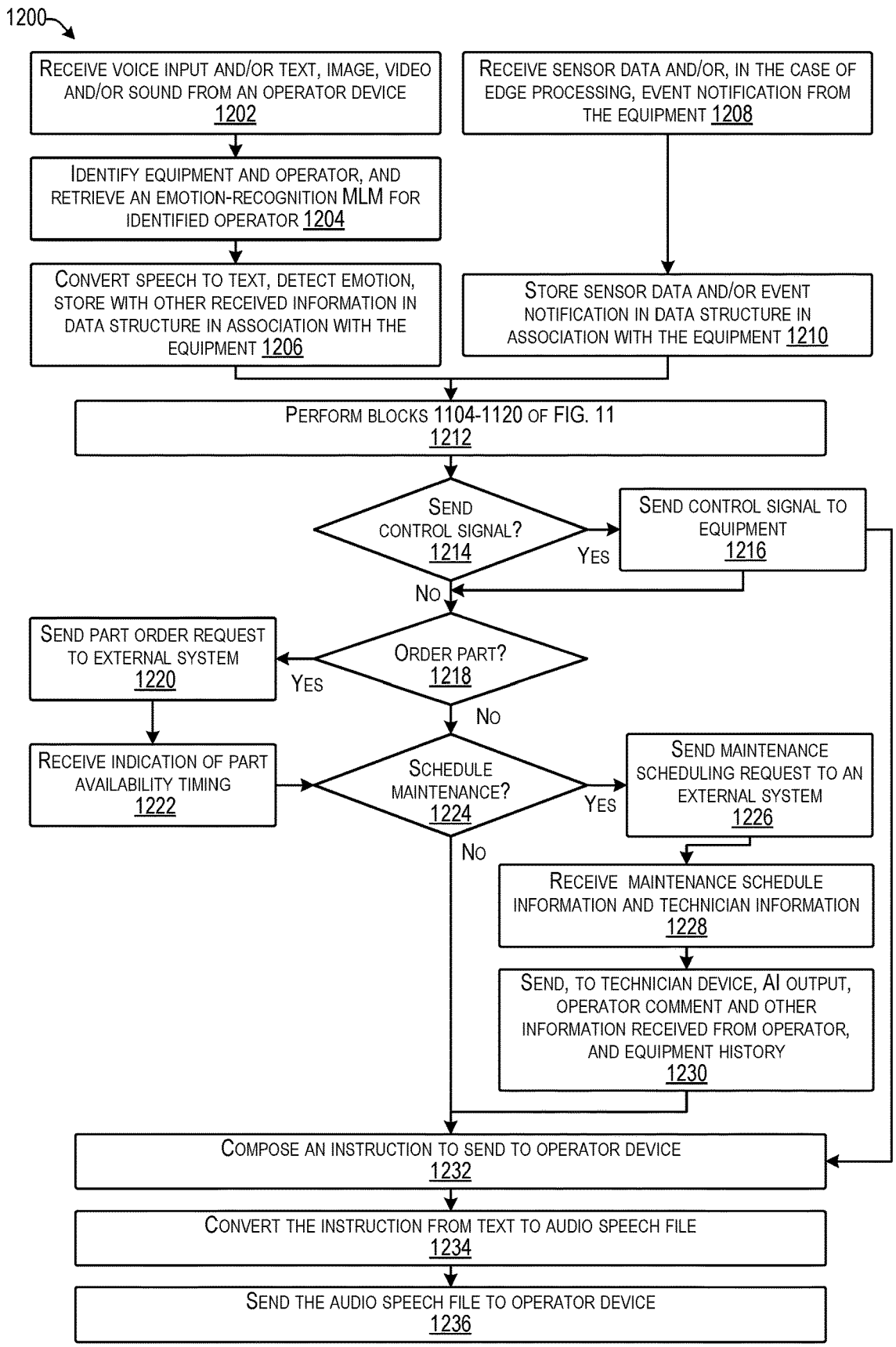
FIG. 12 is a flow diagram illustrating an example process for responding to an input from the operator device or the equipment according to some implementations.

FIG. 12 is a flow diagram illustrating an example process 1200 for responding to an input from the operator device or the equipment according to some implementations. In some examples, the process 1200 may be performed by one or more processors of the service computing device 102 by executing the management program(s) 122 for performing at least some of the operations described in the process 1200.

At 1202, the computing device may receive voice input and/or text, image, video and/or sound from an operator device.

At 1204, the computing device may identify the equipment and the operator, and may retrieve an emotion-recognition MLM for the identified operator. In some examples, the operator device may be associated with the equipment to make identification of the equipment a simple matter of identifying the device sending the voice input. In other examples, however, the equipment might only be identified after identifying the operator and sending a request to an external system computing device, such as a fleet management system to identify the equipment assigned to the identified operator.

At 1206, the computing device may convert speech to text, detect emotion, store with other received information in one or more data structures in association with the equipment.

At 1208, the computing device may receive sensor data and/or, in the case of edge processing, event notification from the equipment.

At 1210, the computing device may store sensor data and/or event notification in data structure in association with the equipment.

At 1212, the computing device may perform blocks 1104-1120 of FIG. 11.

At 1214, the computing device may determine whether to send a control signal to the equipment. For example, if the equipment may be safely controlled remotely, and there is an urgent need to control the equipment, such as for preventing further damage to the equipment, people, or property, the computing device may determine to send a control signal for controlling the equipment.

At 1216, the computing device may send a control signal to control the equipment. In addition, the process may split, and the computing device may also perform the operations of blocks 1232-1236 contemporaneously with sending the control signal to inform the operator of the reason for remotely controlling the equipment. The process may also proceed to block 1218.

At 1218, the computing device may determine whether to order a part for repairing the equipment.

At 1220, if a part is to be ordered for repairing the equipment, the computing device may send a part order request to an external system, e.g., the orders and parts system computing device(s) 236 discussed above with respect to FIG. 2.

At 1222, the computing device may receive an indication of a timing for the part availability, which may be used when scheduling the maintenance for the equipment.

At 1224, the computing device may determine whether to schedule maintenance for the equipment.

At 1226, the computing device may send a maintenance-scheduling request to an external system, such as the fleet management system computing device(s) 232 discussed above with respect to FIG. 2.

At 1228, the computing device may receive maintenance schedule information and technician information.

At 1230, the computing device may send, to the technician device of the scheduled technician, the AI output, operator comment(s) and other information received from the operator, and the equipment history for the equipment for which the maintenance has been scheduled.

At 1232, the computing device may compose an instruction to send to operator device. For example, the instruction may instruct the operator to deliver the equipment for maintenance at the scheduled place and time, or the like.

At 1234, the computing device may convert the instruction from text to audio speech file. For example, the management program(s) may use any conventional text-to-speech programs for converting text to natural language audio.

At 1236, the computing device may send the audio speech file to operator device, which may play or otherwise present the instruction to the operator.

Figure 13:
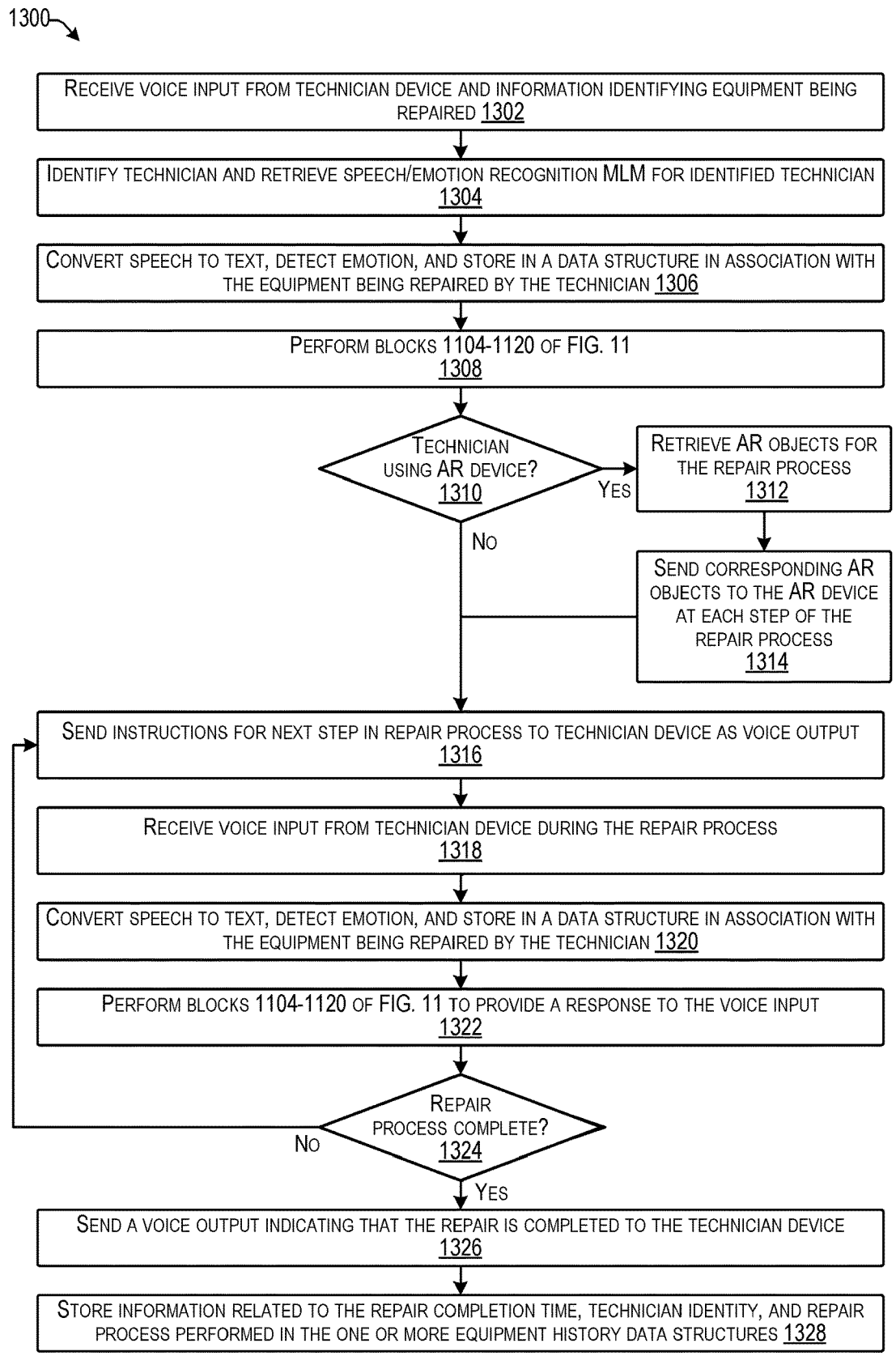
FIG. 13 is a flow diagram illustrating an example process for responding to an input received from a technician device according to some implementations.

FIG. 13 is a flow diagram illustrating an example process 1300 for responding to an input received from a technician device according to some implementations. In some examples, the process 1300 may be performed by one or more processors of the service computing device 102 by executing the management program(s) 122 for performing at least some of the operations described in the process 1300.

At 1302, the computing device may receive a voice input from technician device and information identifying equipment being repaired.

At 1304, the computing device may identify the technician and retrieve the customized speech/emotion recognition MLM previously generated for the identified technician. As one example, the technician may be identified through the client application on the technician device, such as through a login ID, username, or the like.

At 1306, the computing device may convert speech to text, detect emotion, and store in a data structure in association with the equipment being repaired by the technician.

At 1308, the computing device may perform blocks 1104-1120 of FIG. 11 using the input received from the technician device.

At 1310, the computing device may determine whether the technician is using an augmented reality (AR)-capable device. If so, the process goes to 1312. If not, the process goes to 1316. As one example, the computing device may communicate with the client application executing on the technician device to determine the AR capabilities of the technician device.

At 1312, the computing device may retrieve AR objects for the repair process. For example, the AR objects may have been generated in advance for the repair process to be performed by the technician. Examples of AR objects may include AR text, AR 2D and 3D images, AR video, and so forth, for providing instructions during some or all of the steps of the repair.

At 1314, the computing device may send corresponding AR objects to the AR device at each step of the repair process.

At 1316, the computing device may send instructions for the next step in the repair process to the technician device as voice output. Additionally, the computing device may also send images, text, video, AR objects, and the like for providing detailed instructions for each step of the repair process.

At 1318, the computing device may receive voice input from technician device during the repair process.

At 1320, the computing device may convert speech to text, detect emotion, and store in a data structure in association with the equipment being repaired by the technician 1320

At 1322, the computing device may perform blocks 1104-1124 of FIG. 11 using the input received from the technician device to provide a response, such as a voice output, in response to the voice input.

At 1324, the computing device may determine whether the repair process is complete. If so, the process goes to 1326. If not, the process goes to 1316 to send the next step in the repair process to the technician as a voice output.

At 1326, based on determining that the repair process is complete, the computing device may send a voice output indicating that the repair is completed to the technician device.

At 1328, the computing device may store information related to the repair completion time, technician identity, and repair process performed in the one or more equipment history data structures. Accordingly, the system herein provides an integrative system that accesses an artificial intelligence service that executes one or more machine learning models to determine instructions for predictive maintenance and/or repair of the equipment. Further, the system may integrate information received from one or more external computing devices, information received from the equipment and/or the equipment operator, and information received from an equipment repair site to enable a seamless end-to-end user experience for determining one or more instructions for maintenance and/or repair.

Figure 14:
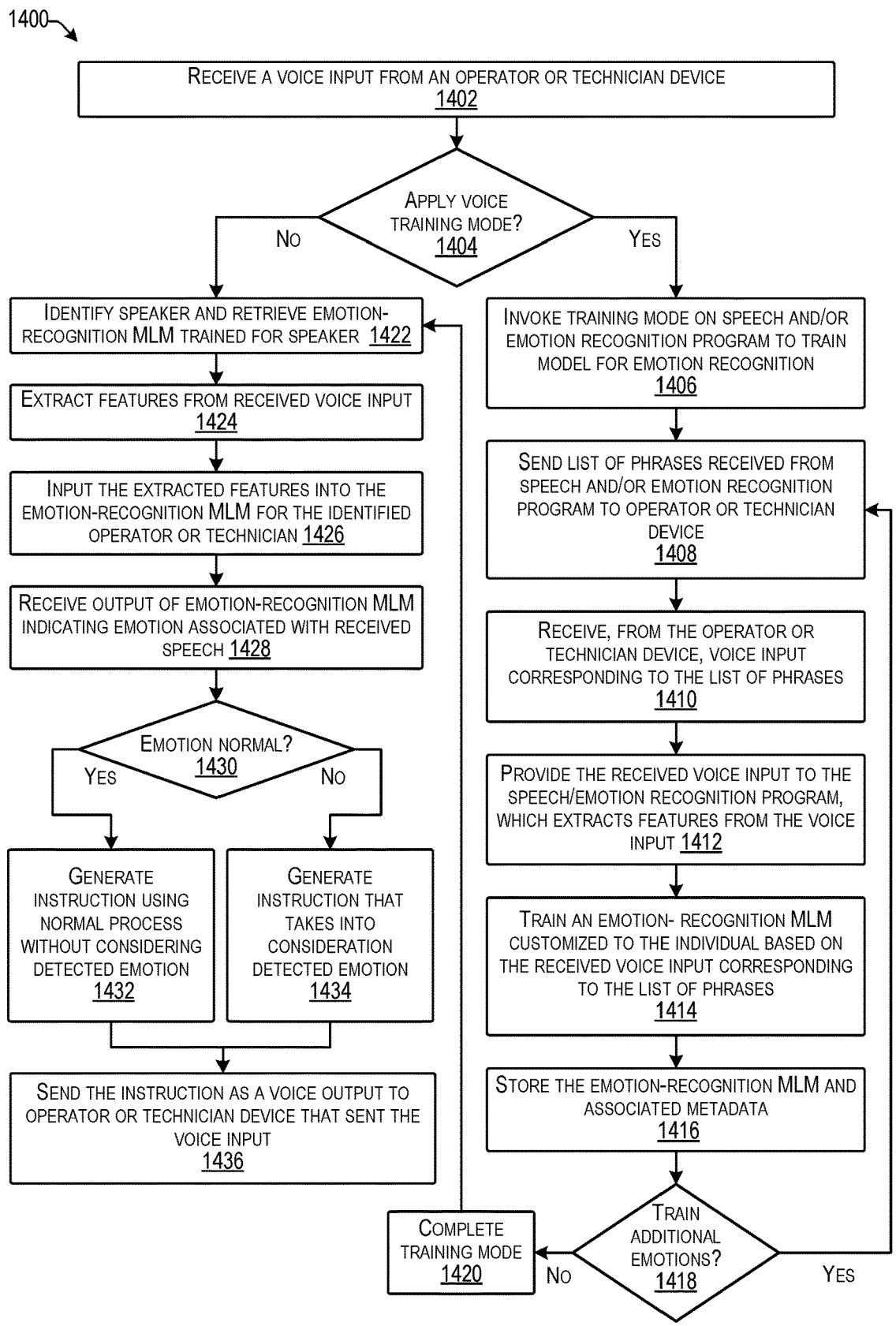
FIG. 14 is a flow diagram illustrating an example process for detecting emotions in received voice inputs according to some implementations.

FIG. 14 is a flow diagram illustrating an example process 1400 for detecting emotions in received voice inputs according to some implementations. In some examples, the process 1400 may be performed by one or more processors of the service computing device 102 by executing the management program(s) 122, which may invoke the speech and/or emotion recognition program 128 for performing at least some of the operations described in the process 1400.

At 1402, the computing device may receive a voice input from operator or technician device.

At 1404, the computing device may determine whether to apply a voice training mode. For example, the computing device may determine an identity of person providing the voice input, and may determine whether there is an existing emotion-recognition machine learning model (MLM) for that person. If so, the process goes to 1422. If not, the process goes to 1406.

At 1406, the computing device may invoke training mode on the speech and/or emotion recognition program to train a model for emotion recognition for the particular person.

At 1408, the computing device may send a list of phrases received from speech and/or emotion recognition program to the operator or technician device. The list of phrases may instruct the individual to say each of the phrases in several different ways, such as normal, and also with anger, frustration, or other non-normal emotions.

At 1410, the computing device may receive, from the operator or technician device, voice input corresponding to the list of phrases.

At 1412, the computing device may provide the received voice input to the speech/emotion recognition program, which extracts features from the voice input.

At 1414, the computing device may train an emotion recognizing MLM customized to the individual based on the received voice input corresponding to the list of phrases. For example, the extracted features may be used to train the emotion recognizing MLM for the individual.

At 1416, the computing device may store the emotion-recognition MLM and associated metadata.

At 1418, the computing device may determine whether the training is complete, or if there are additional emotions to be trained. If the training is not complete, the process may return to 1408 to send additional phrases and instructions to the device. If the training is complete, the process goes to 1420.

At 1420, the computing device may determine that the training is complete, and the model may be used for emotion recognition for the individual.

At 1422, the computing device may identify the speaker and retrieve the corresponding emotion-recognition MLM for the identified individual.

At 1424, the computing device may extract features from the received voice input.

At 1426, the computing device may input the extracted features into the emotion-recognition MLM for the identified operator or technician.

At 1428, the computing device may receive output of emotion-recognition MLM indicating emotion associated with received speech.

At 1430, the computing device may determine whether the output of the emotion-recognition MLM indicates a normal emotional state. For example, non-normal emotional states may include anger, frustration, anxiety, or the like.

At 1432, the computing device may generate an instruction using normal process without considering detected emotion.

At 1434, the computing device may generate an instruction that takes into consideration the detected non-normal emotion. Examples are discussed above with respect to FIG. 1.

At 1436, the computing device may send the instruction as a voice output to the operator or technician device that sent the voice input.

The example processes described herein are only examples of processes provided for discussion purposes. Numerous other variations will be apparent to those of skill in the art in light of the disclosure herein. Further, while the disclosure herein sets forth several examples of suitable systems, architectures and environments for executing the processes, the implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Various instructions, processes, and techniques described herein may be considered in the general context of computer-executable instructions, such as programs stored on computer-readable media, and executed by the processor(s) herein. Generally, programs include routines, modules, objects, components, data structures, executable code, etc., for performing particular tasks or implementing particular abstract data types. These programs, and the like, may be executed as native code or may be downloaded and executed, such as in a virtual machine or other just-in-time compilation execution environment. Typically, the functionality of the programs may be combined or distributed as desired in various implementations. An implementation of these programs and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed:

1. A system comprising:
   one or more processors; and
   one or more non-transitory computer-readable media maintaining executable instructions, which, when executed by the one or more processors, configure the one or more processors to perform operations comprising:
   storing, for a plurality of users, a plurality of respective emotion-recognition machine learning models, each respective emotion recognition machine learning model trained by a different person to be customized for the person who trained the respective emotion recognition machine learning model;
   receiving from a device, a voice input including a comment related to equipment;
   determining an identity of a person associated with the device;

identifying the equipment related to the comment;
based on determining the identity of the person associated with the device, retrieving, for responding to the voice input, one of the plurality of respective emotion-recognition machine learning models, the retrieved respective emotion-recognition machine learning model determined to have been trained by the identified person;
using the retrieved emotion-recognition machine learning model customized for the identified person to determine whether an emotion classification associated with the voice input is classified as normal or non-normal;
converting the voice input to text and providing the text and an indication of the emotion classification as input to one or more additional machine learning models to determine, at least in part, a response to the voice input for instructing at least one of a repair or maintenance action for the equipment, wherein a first repair or maintenance action for the equipment is determined based on the emotion classification being classified as normal, and a second, different repair or maintenance action for the equipment is determined based on the emotion classification being classified as non-normal;
composing a text instruction for responding to the voice input based on the determined response to the voice input;
converting the text instruction to an audio speech file;
sending the audio speech file to the device for presentation on the device;
determining whether the device is an augmented reality (AR)-capable device; and
based on determining that the device is AR-capable, sending one or more augmented reality (AR) objects to the device in association with the instruction sent to the device, the one or more AR objects including one or more images related to the equipment.

2. The system as recited in claim 1, wherein the device is associated with an operator of the equipment, and the voice input is received from the operator, the operations further comprising:
receiving at least one of sensor data or an event notification from the equipment indicating a condition of the equipment based on at least one sensed parameter; and
providing at least one of: the sensor data, the event notification, or an indication of the condition of the equipment to the one or more additional machine learning models when determining the response to the voice input.

3. The system as recited in claim 2, the operations further comprising:
based at least in part on the response, determining to remotely control the equipment; and
sending a control signal to the equipment to remotely control the equipment based at least in part on the at least one of the received sensor data or the event notification.

4. The system as recited in claim 1, the operations further comprising, based at least in part on determining that the emotion classification is non-normal, performing at least one of:
sending a request to an external system computing device to assign a technician having a higher skill level than other technicians available for performing a repair to the equipment;
connecting the operator in a direct voice communication with a technician; or
providing, with the instruction in the audio speech file, a detailed explanation of a determined problem and/or operational guidance for managing the equipment.

5. The system as recited in claim 1, the operations further comprising, based at least in part on the response to the voice input, performing at least one of:
sending, to an external computing device, a request to order a part for repairing the equipment; or
sending, to an external computing device, a request to schedule at least one of a technician or a repair site for repairing the equipment.

6. The system as recited in claim 5, wherein the executable instructions further configure the one or more processors to integrate information received from one or more of the external computing devices, information received from the equipment and/or an equipment operator, and information received from an equipment repair site to enable a seamless end-to-end user experience for providing one or more instructions for maintenance and/or repair.

7. The system as recited in claim 5, the operations further comprising, based at least in part on a timing for receiving the part, or a timing for scheduling the at least one of the technician or the repair site, including in the instruction an indication of a timing for the repair of the equipment.

8. The system as recited in claim 1, wherein the device is associated with a technician for repairing the equipment, and the voice input is received from the technician, the operations further comprising sending, to the device, information received from an operator of the equipment, an equipment history for the equipment, and sensor data received from the equipment.

9. The system as recited in claim 1, wherein the device is associated with a technician for repairing the equipment, and the voice input is received from the technician, the operations further comprising:
sending a plurality of the instructions to the device to provide step-by-step verbal instructions to the technician during repair of the equipment; and
sending the one or more AR objects to the device in association with one or more instructions of the plurality of instructions sent to the device, the one or more AR objects including at least one three-dimensional model related to the equipment.

10. The system as recited in claim 1, wherein the executable instructions further configure the one or more processors as an integrative system that accesses an artificial intelligence service that executes the emotion-recognition machine learning model and/or the one or more additional machine learning models to provide instructions for predictive maintenance and/or repair of the equipment.

11. A method comprising:
receiving, by one or more processors, from a device, speech sound patterns corresponding to a voice input related to equipment;
determining an identity of a person associated with the device;
identifying the equipment related to the voice input;
using an emotion-recognition machine learning model customized for the identified person to determine whether an emotion classification associated with the voice input is classified as normal or non-normal;
using at least one of the received speech sound patterns or a text conversion of the speech sound patterns, along with an equipment history of the identified equipment and the determined emotion classification, as input to one or more machine learning models to determine, at least partially, an instruction related to the equipment for instructing at least one of a repair or maintenance action for the equipment, wherein a first repair or maintenance action for the equipment is determined based on the emotion classification being classified as normal, and a second, different repair or maintenance action for the equipment is determined based on the emotion classification being classified as non-normal;

sending, to the device, the instruction related to the equipment as an audio file for playback on the device;

determining, by the one or more processors, whether the device is an augmented reality (AR)-capable device; and based on determining that the device is AR-capable, sending one or more augmented reality (AR) objects to the device in association with the instruction sent to the device, the one or more AR objects including one or more images related to the equipment.

12. The method as recited in claim 11, wherein the equipment is not the device from which the voice input is received, and wherein identifying the equipment related to the voice input further comprises determining the identity of the equipment from the voice input.

13. The method as recited in claim 11, further comprising:

storing, for a plurality of users, a plurality of respective emotion-recognition machine learning models, each respective emotion recognition machine learning model trained by a different person to be customized for the person who trained the respective emotion recognition machine learning model, wherein training the respective emotion-recognition machine learning model includes having each different person say phrases with a plurality of different emotions.

14. The method as recited in claim 11, wherein the device is associated with an operator of the equipment, and the voice input is received from the operator, the operations further comprising:

receiving at least one of sensor data or an event notification from the equipment indicating a condition of the equipment based on at least one sensed parameter; and providing at least one of: the sensor data, the event notification, or an indication of the condition of the equipment to the one or more machine learning models when determining the instruction related to the equipment.

15. The method as recited in claim 11, wherein the device is associated with a technician for repairing the equipment, and the voice input is received from the technician, the operations further comprising sending a plurality of the instructions to the device to provide step-by-step verbal instructions to the technician during repair of the equipment; and sending the one or more AR objects to the device in association with one or more instructions of the plurality of instructions sent to the device, the one or more AR objects including at least one three-dimensional model related to the equipment.

16. The method as recited in claim 11, further comprising:

associating the person with the equipment in advance of receiving the voice input, wherein the equipment is not the device from which the voice input is received;

determining the identity of a person associated with an application executing on the device; and sending a request to an external system computing device to determine the identity of the equipment associated with the person.

17. The method as recited in claim 11, further comprising integrating information received from one or more external computing devices, information received from the equipment and/or an equipment operator, and information received from an equipment repair site to enable a seamless end-to-end user experience for providing one or more instructions for maintenance and/or repair.

18. The method as recited in claim 11, wherein the one or more processors operate as an integrative system that accesses an artificial intelligence service that executes one or more machine learning models to provide instructions for predictive maintenance and/or repair of the equipment.

19. One or more non-transitory computer-readable media storing instructions which, when executed by one or more processors, program the one or more processors to perform operations comprising:

receiving, from a device, speech sound patterns corresponding to a voice input related to equipment;

determining an identity of a person associated with the device;

identifying the equipment related to the voice input;

using an emotion-recognition machine learning model customized for the identified person to determine whether an emotion classification associated with the voice input is classified as normal or non-normal;

using at least one of the received speech sound patterns or a text conversion of the speech sound patterns, along with an equipment history of the identified equipment and the determined emotion classification, as input to one or more machine learning models to determine, at least partially, an instruction related to the equipment for instructing at least one of a repair or maintenance action for the equipment, wherein a first repair or maintenance action for the equipment is determined based on the emotion classification being classified as normal, and a second, different repair or maintenance action for the equipment is determined based on the emotion classification being classified as non-normal;

sending, to the device, the instruction related to the equipment as an audio file for playback on the device;

determining whether the device is an augmented reality (AR)-capable device; and based on determining that the device is AR-capable, sending one or more augmented reality (AR) objects to the device in association with the instruction sent to the device, the one or more AR objects including one or more images related to the equipment.

20. The one or more non-transitory computer-readable media as recited in claim 19, wherein:

a plurality of respective emotion-recognition machine learning models are stored for a plurality of users, respectively, each respective emotion recognition machine learning model trained by a different person to be customized for the person who trained the respective emotion recognition machine learning model; and training the respective emotion-recognition machine learning model includes having each different person say phrases with a plurality of different emotions.

21. The one or more non-transitory computer-readable media as recited in claim 19, wherein the device is associated with an operator of the equipment, and the voice input is received from the operator, wherein the one or more processors are further programmed to perform operations comprising:

receiving at least one of sensor data or an event notification from the equipment indicating a condition of the equipment based on at least one sensed parameter; and providing at least one of: the sensor data, the event notification, or an indication of the condition of the equipment to the one or more machine learning models when determining the instruction related to the equipment.

22. The one or more non-transitory computer-readable media as recited in claim 21, wherein the one or more processors are further programmed to perform operations comprising:

based at least in part on the instruction, determining to remotely control the equipment; and sending a control signal to the equipment to remotely control the equipment based at least in part on the at least one of the received sensor data or the event notification.

23. The one or more non-transitory computer-readable media as recited in claim 19, wherein the device is associated with a technician for repairing the equipment, and the voice input is received from the technician, wherein the one or more processors are further programmed to perform operations comprising:

sending a plurality of the instructions to the device to provide step-by-step verbal instructions to the technician during repair of the equipment; and sending the one or more AR objects to the device in association with one or more instructions of the plurality of instructions sent to the device, the one or more AR objects including at least one three-dimensional model related to the equipment.

24. The one or more non-transitory computer-readable media as recited in claim 19, wherein the one or more processors are further programmed to integrate information received from one or more external computing devices, information received from the equipment and/or an equipment operator, and information received from an equipment repair site to enable a seamless end-to-end user experience for providing one or more instructions for maintenance and/or repair.

25. The one or more non-transitory computer-readable media as recited in claim 19, wherein the one or more processors are further programmed to operate as an integrative system that accesses an artificial intelligence service that executes one or more machine learning models to provide instructions for predictive maintenance and/or repair of the equipment.

* * * * *